United States Patent [19]

Lambelin et al.

[11] Patent Number: 4,638,070

[45] Date of Patent: Jan. 20, 1987

[54] HETEROCYCLIC AMINO-ALCOHOL DERIVATIVES

[75] Inventors: Georges E. Lambelin, Brussels; Roméo R. Roncucci, Rosières-St-André; Joseph Roba, Wanlin; Claude L. Gillet, Brussels, all of Belgium

[73] Assignee: Continental Pharma, Brussels, Belgium

[21] Appl. No.: 164,326

[22] Filed: Jun. 30, 1980

Related U.S. Application Data

[63] Continuation of Ser. No. 971,715, Dec. 21, 1978, abandoned, which is a continuation-in-part of Ser. No. 742,917, Nov. 17, 1976, abandoned.

[51] Int. Cl.$^4$ .................. C07D 337/00; C07D 327/06; C07D 333/52; C07D 335/04
[52] U.S. Cl. ....................................... 549/23; 549/58; 549/9
[58] Field of Search ................... 549/9, 15, 49, 23, 58

[56] References Cited

U.S. PATENT DOCUMENTS

| | | | |
|---|---|---|---|
| 3,255,249 | 6/1966 | Howe et al. ..................... | 260/563 R |
| 3,903,092 | 9/1975 | Chapman et al. ................ | 260/330.5 |
| 3,928,358 | 12/1975 | Renth et al. ........................ | 544/377 |

FOREIGN PATENT DOCUMENTS

| | | | |
|---|---|---|---|
| 1532210 | 4/1964 | France . | |
| 2138488 | 5/1973 | France ............................... | 260/563 |
| 2241315 | 9/1975 | France . | |
| 8895676 | 8/1976 | Japan ..................................... | 549/9 |
| 1013224 | 12/1965 | United Kingdom .................... | 549/9 |
| 1019772 | 2/1966 | United Kingdom .................... | 549/9 |

OTHER PUBLICATIONS

Chem. Abst., vol. 61, 5580b (1964).
Chem. Abst., vol. 61, 625d (1964).
Chem. Abst., vol. 61, 672h (1964).
Chem. Abst., vol. 62, 16162c (1965).
Chem. Abst., 64, 2101c (1966).
Chem. Abst., 65, 15294d (1966).
Chem. Abst., 67, 82119r (1967).
Chem. Abst., 68, 21764w (1968).
Chem. Abst., 76, 3597c (1972).
Chem. Abst., 82, 155920s (1975).
Chem. Abst., 82, 171,049u (1975).
M. S. Chodnekar et al., β-Adrenergic Blocking Agents, Journal of Med. Chem., vol. 15, No. 1, pp. 49-57.
Chem. Abst., 68, 21743p (1968).
Chem. Abst., 71, 74025z (1969).
Chem. Abst., 75, 76464y (1971).
Chem. Abst., 76, 3594b (1972).
Chem. Abst., 70, 37547e (1969).
Chem. Abst., 71, 42314b (1969).
Chem. Abst., 71, 74088x (1969).
Chem. Abst., 75, 76474b (1971).
Chem. Abst., 82, 155916v (1975).
Chem. Abst., 82, 171,056v (1975).
Troxler et al., Hebv. Chim. Acta, vol. 51, pp. 1616 to 1628 (1968).
Pfleger et al., Chem. Ber., vol. 90, pp. 1500 to 1512 (1957).
Casagrande et al., Chem. Abst., vol. 64, col. 19509, et seq. (1966).
Hofmann, Chem. Abst., vol. 70, abst. 37541y (1969).

*Primary Examiner*—Henry R. Jiles
*Assistant Examiner*—Robert C. Whittenbaugh
*Attorney, Agent, or Firm*—Stevens, Davis, Miller & Mosher

[57] ABSTRACT

This invention relates to heterocyclic amino-alcohol derivatives of the formula

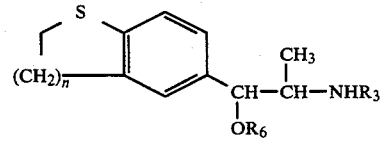

These compounds are useful as antihypertensives.

4 Claims, No Drawings

HETEROCYCLIC AMINO-ALCOHOL DERIVATIVES

This is a continuation of application Ser. No. 971,715 filed Dec. 21, 1978, now abandoned which in turn is a continuation of application Ser. No. 742,917 filed Nov. 17, 1976, now abandoned.

This invention relates to heterocyclic amino-alcohol derivatives including substituted amino-alcohols, esters of these amino-alcohols and salts thereof, to their preparation, to pharmaceutical compositions containing at least one of said derivatives, as well as to use thereof.

Derivatives according to the invention have the following general formula:

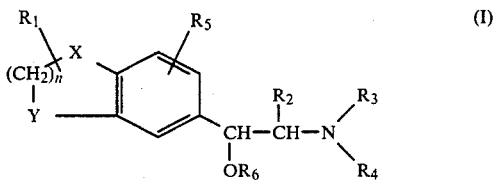

wherein:

(a) $R_1$ represents hydrogen, one or two linear or ramified alkyl radicals $(C_1-C_3)$, a phenyl radical or a carboxy radical;

(b) $R_2$ is a linear or ramified alkyl radical $(C_1-C_3)$;

(c) $R_3$ is:
  a mono or polyunsaturated alkenyl radical $(C_3-C_{18})$
  a mono or polyunsaturated alkenyl radical $(C_3-C_{12})$ substituted by oxygen, sulfur or a phenyl radical;
  a mono or polyunsaturated alkynyl radical $(C_3-C_{18})$;
  a mono or polyunsaturated alkynyl radical $(C_3-C_{12})$ substituted by oxygen, sulfur or a phenyl radical;
  a cycloalkyl radical $(C_3-C_{10})$;
  a linear or ramified alkyl radical $(C_2-C_{20})$;
  a linear or ramified alkyl radical $(C_2-C_{18})$ substituted by at least an atom and/or radical selected from the group comprising:
   (1) oxygen or sulfur,
   (2) alkoylcarbonyl radicals $(C_1-C_3)$, pyrrolidine, pyrrolidinone or imidazolidone,
   (3) phenyl, phenoxy, phenylthio, benzoyl, indanyloxy, naphtyloxy radicals
   (4) phenyl, phenoxy, phenylthio, benzoyl radicals substituted by one or more alkyl$(C_1-C_4)$ or alkoxy$(C_1-C_4)$ radicals, by one or two halogen atoms, by a nitrile, hydroxy, amino alkanoyl($C_2-C_6$), acylamino$(C_2-C_4)$, alkoxycarbonyl$(C_1-C_4)$ or alkylsulfonamido$(C_1-C_4)$ radical, (d) $R_4$ is hydrogen or when taken with $R_3$ and adjacent nitrogen atom, they form a morpholine, pyrrolidine, piperidine radical or a piperidine radical substituted by one or two alkyl$(C_1-C_4)$ phenyl or phenylalkyl$(C_1-C_4)$ radicals, or a piperazine radical substituted in position 4 by a phenyl radical or by a phenyl radical itself substituted by (1) one or two alkyl$(C_1-C_4)$ or alkoxy$(C_1-C_4)$ radicals, (2) one or two halogen atoms, or (3) a trifluoromethyl radical;

(e) $R_5$ is hydrogen or an alkyl$(C_1-C_3)$ radical;

(f) $R_6$ is hydrogen or a linear or ramified alkanoyl($C_1-C_{10}$) radical or a cycloalkanoyl$(C_3-C_8)$ radical;

(g) n is equal to 1, 2 or 3;

(h) X is sulfur, oxygen, a $CH_2$ radical or a NH radical;

(i) Y is a $CH_2$ radical or sulfur;

(j) when simultaneously X is oxygen, Y is a $CH_2$ group, n is equal to 2, $R_1$ and $R_5$ are hydrogen, $R_2$ is methyl and $R_6$ is hydrogen or an alkanoyl radical, $R_4$ does not form a substituted piperazine radical with $R_3$ and adjacent nitrogen atom.

This invention advantageously includes derivatives of formula I, wherein:

(a) $R_1$ is hydrogen or an alkyl$(C_1-C_3)$ radical;
(b) $R_2$ is an alkyl$(C_1-C_3)$ radical;
(c) $R_3$ is:
  a mono or polyunsaturated alkenyl$(C_3-C_{18})$ radical;
  a mono or polyunsaturated alkynyl$(C_3-C_{18})$ radical;
  a cycloalkyl$(C_3-C_8)$ radical;
  an alkyl$(C_2-C_{18})$ radical;
  an alkyl$(C_2-C_{16})$ radical substituted by (1) a phenylthio radical, an alkoxy$(C_1-C_6)$ radical, an alkylthio$(C_1-C_6)$ radical, a phenoxy radical, a benzoyl radical, one or two phenyl radicals, (2) a phenyl, benzoyl, phenylthio or phenoxy radical each substituted by an alkyl$(C_1-C_3)$ or a halogen, (3) a phenoxy radical substituted by a nitrile or a alkanoyl($C_2-C_3$) radical;

(d) $R_4$ is hydrogen or when considered with $R_3$ and adjacent nitrogen atom, they form (1) a piperazine radical substituted by a phenyl radical which is in turn substituted by an alkyl$(C_1-C_3)$ radical, (2) a piperidine radical substituted by an alkyl$(C_1-C_3)$ radical which is itself substituted by a phenyl radical;

(e) $R_5$ is hydrogen or an alkyl$(C_1-C_3)$ radical;
(f) $R_6$ is hydrogen, a linear or ramified alkanoyl($C_1-C_8$) radical or a cycloalkanoyl$(C_3-C_6)$ radical;
(g) n is equal to 1, 2 or 3;
(h) X is sulfur, oxygen or an NH radical;
(i) Y is a $CH_2$ radical or sulfur.

A preferred class of compounds according to formula I comprises those compounds wherein $R_1$ is hydrogen or methyl, $R_2$ is methyl or ethyl, $R_3$ is an alkyl$(C_2-C_{18})$ radical, an alkyl$(C_2-C_{10})$ radical substituted by (1) a phenyl, phenylthio phenoxy or benzoyl radical or (2) a phenyl, phenylthio, phenoxy or benzoyl radical each substituted by one or two alkyl$(C_1-C_3)$ radicals or halogen, $R_4$ and $R_5$ are hydrogen, $R_6$ is hydrogen, an alkanoyl$(C_1-C_4)$ radical or a cycloalkanoyl$(C_3-C_6)$ radical, n is equal to 1,2 or 3, X is sulfur and Y is $CH_2$.

Examples of derivatives according to the invention are:
1-(6-thiochromanyl)-2-n-octylamino-1-propanol
1-(6-thiochromanyl)-2-(4-phenylbutylamino)-1-propanol
1-(6-thiochromanyl)-2-[2-(phenoxy)ethylamino]-1-propanol
1-(2,3-dihydro-5-benzo[b]thienyl)-2-n-octylamino-1-propanol
1-(2,3-dihydro-5-benzo[b]thienyl)-2-(4-phenylbutylamino)-propanol
1-(2,3-dihydro-5-benzo[b]thienyl)-2-[4-(p-chlorophenyl)butylamino]-1-propanol
1-(2-methyl-2,3-dihydro-5-benzo[b]thienyl)-2-(4-phenylbutylamino)-1-propanol
1-(2-methyl-2,3-dihydro-5-benzo[b]furanyl)-2-n-octylamino-1-propanol
1-(2,3,4,5-tetrahydrobenzo[b]thiepin-7-yl)-2-(4-phenylbutylamino)-1-propanol
1-(2,3-dihydro-5-indolyl)-2-n-octylamino-1-propanol
1-(2,3-dihydro-5-benzo[b]thienyl)-2-(4-phenylbutylamino)-1-propionyloxypropane.

1-(2,3-dihydro-5-benzo[b]thienyl)-2-(4-phenyl-butylamino)-1-cyclohexanoyloxypropane
1-(5-indanyl)-2-(4-phenylbutylamino)-1-propanol
1-(5-indanyl)-2-[2-(4-chlorophenoxy)ethylamino]-1-propanol
1-(5-indanyl)-2-[2-(4-fluorobenzoyl)propylamino]-1-propanol Derivatives according to formula I which can exist as salts are more particularly salts of inorganic acids, such as hydrochloride, phosphates, sulfates, or salts of organic acids, such as oxalates, lactates, tartarates, acetates, citrates, maleate glucuronates, gluconates.

The more active products according to the invention having two asymetry centers, two racemates can be obtained corresponding to erythro and threo configurations respectively: both said racemates can be resolved by conventional methods, for example by forming diastereoisomer salts by action of optically active acids, such as tartaric, diacetyltartaric, tartranilic, dibenzoyltartaric, ditoluoyltartaric acids, and separation of the diastereoisomer mixture by crystallization, distillation, chromatography, then liberation of optically active bases from said salts.

The same processes can be used when compounds according to the invention comprises more than two asymetry centers.

The more active derivatives of the invention can thus be used either as racemates of configuration erythro or threo or as a mixture of these forms, or still as optically active compounds of each of both said forms.

In general, amino-alcohol derivatives according to the invention have some activities on the cardiovascular system, such as antihypertensive and/or antispasmodic activities, a peripheral vasodilator activity, a protecting activity against myocaranoxy, hypolipidemic, antithrombotic, β-lytic activities, a platelet-aggregation inhibitory activity and/or activities on the central nervous system, for example a tranquillizing activity.

These properties allow to comtemplate use of the products according to the invention in the treatment of hypertension and cardiovascular diseases, such as atherosclerosis.

More particularly, it has been found that derivative according to the invention are endowed inter alia with very high antihypertensive, hypolipi emic and antithrombotic activities.

Active compounds according to the invention can be administered in association with various pharmaceutical excipients, orally or parenterally.

For oral administration, coated pills, granules, tablets, capsules, solutions, syrups, emulsions and suspensions will be used, containing additives and excipients which are usual galenic pharmacy. For parenteral administration, a liquid such as sterile water or an oil, such as peanut oil or ethyl oleate, will be used.

These active compounds can be used alone or in combination with other active products having a similar or different activity.

The new compounds according to the invention are prepared following the general process forming also a part of the invention and defined as follows.

The new derivatives are prepared from a compound having formula(II):

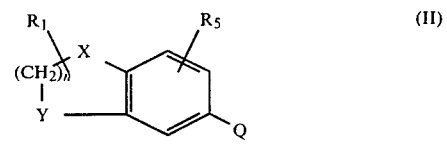

or optionally, according to the meaning of Q, from a salt of a compound of this formula (II), wherein $R_1$, $R_5$, Y, X and n have the hereinabove mentioned meaning Q represents one of the following groups:

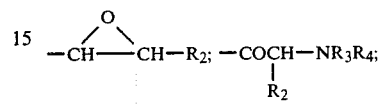

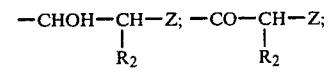

In these groups, $R_2$, $R_3$ and $R_4$ have also the meaning such as mentioned hereinbefore, while z is a halogen atom, such as Cl or Br.

This general process can be carried out according to two methods which are essentially determined by the starting product, namely by the meaning of Q in formula (II).

According to a first preparation method, a α-aminoketone having formula (II) in which Q represents a group

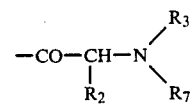

$R_2$ and $R_3$ having the meaning such as already mentioned, $R_7$ has the meaning of $R_4$ or is a protecting group which can be removed later by hydrolysis or hydrogenolysis, such as benzyl, trityl, acetyl, formyl, benzhydryl groups is reduced.

This reduction can be made in an usual manner, most easily for example by action of alkali metal hydrides, such as sodium borohydride, in a solvent such as methanol or ethanol, preferably at low temperature or aluminum and lithium hydride in a solvent such as diethyl ether or tetrahydrofuran, or also by action of an aluminium alkoxide, such as aluminum isopropoxide, in a solvent such as isopropanol, most advantageously at reflux thereof. The reduction can also be made by hydrogenation in the presence of a catalyst, such as palladium on carbon, Raney nickel, platinum oxide in a solvent, such as methanol, ethanol, dioxan, acetic acid.

As mentioned before, the most interesting products of the invention can have two configurations, namely erythro and threo. The selection of the starting aminoketone and of reduction conditions allow to obtain either of these two forms stereo selectively. Thus reduction of an aminoketone in which

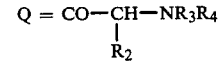

and R₄=hydrogen leads to a compound with erythro configuration under the general conditions hereinbefore described.

In order to obtain a compound with threo configuration, reduction is made on an aminoketone in which

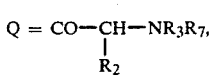

where $R_2$ and $R_3$ have the hereinbefore defined meaning and $R_7$ is a protecting group which can be removed later by hydrolysis or hydro genolysis, such as benzyl, trityl, acetyl, formyl, benzhydryl groups. This reduction is then preferably made by action of alkali metal hydrides, such as sodium borohydride, or aluminum and lithium hydride.

Starting aminoketones are easily obtainable, for example by action of an amino $R_3R_4NH$ on a α-halogenoketone in solvents such as ether, benzene, chloroform, dioxan, methanol, isopropanol or acetonitrile.

It is however well known in the literature that a reaction of this kind generally gives low yields, this being due to formation of many secondary products and to instability of α-aminoketones. According to this invention, a synthesis method has been studied allowing to obtain amino-alcohols of general structure (I) with excellent yields, this being obtained preferably without isolating intermediate aminoketone; a particularly good solvent for this type of reaction reveals to be an alcohol, such as methanol, ethanol or isopropanol. In this connection, according to the invention, a α-halogenoketone of formula (II) wherein

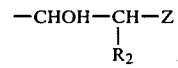

is reacted with an amine $R_3R_4NH$, so as to obtain an aminoketone corresponding to formula (II) where

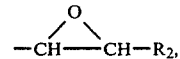

and this aminoketone is reduced as hereinbefore without being previously isolated.

According to a second preparation method, a compound of general formula (II) wherein Q is a group

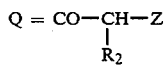

is reacted with an amine of the kind $R_3R_4NH$, in which formulas $R_2$ to $R_4$ and Z have the hereinbefore defined meaning.

This reaction is carried out in a solvent, such as alcohols, chloroform, dioxan, carbon tetrachloride, most easily in the presence of an agent able to capture formed hydrogen halide, such as tertiary inorganic or organic bases or in the presence of excess amine. It is well known that in these cases, the group

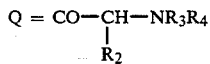

first produces an oxirane of the type

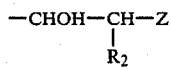

which reacts with the amino compound.

The present process thus also includes preparation of amino-alcohols from oxiranes; this process can advantageously be used for preparing amino-alcohol derivatives having threo configuration.

Salts of amino-alcohols of formula (II) can be prepared, according to the invention, as previously mentioned by the general process such as hereinbefore described.

This process allows several variants. Generally, these salts can be formed by well known methods of this general process, such as for example reaction of equimolecular amounts of the amino-alcohol with an acid in a suitable solvent, such as an alcohol for example, then precipitation of the salt by addition of another solvent which is miscible with the first one and in which the salt is insoluble, for example ether, or also by neutralisation of an ethereal solution of the acid or base with the base or acid. Acids which are used are as well organic as inorganic acids. An inorganic acids, one preferably uses hydrochloric acid, hydrobromic acid, sulfuric acid, phosphoric acid, perchloric acid, and the like.

Organic acids are carboxylic acids or sulfonic acids, such as formic, propionic, glycollic, lactic, citric, ascorbic, fumaric, maleic, pamoic, succinic, tartaric, phenylacetic, benzoic, p-aminobenzoic, anthranilic, p-hydroxybenzoic, salicylic, glucuronic acids and the like.

Esters of amino-alcohols according to formula I, where $R_6$ is an alkanoyl or cycloalkanoyl radical are prepared by reacting an amino-alcohol or a salt thereof with excess of suitable acid chloride or anhydride preferably at a temperature between 50° C. and reflux temperature of acid chloride or anhydride.

According to another method, an amino-alcohol or a salt thereof is reacted with an equimolecular amount or a slight excess of suitable acid chloride or anhydride, for example in a solvent such as acetonitrile, benzene and toluene.

Hereinafter some detailed examples are given relating to the preparation of amino-alcohol derivatives according to the invention. These examples have more particularly for their object to more completely illustrate the particular features of the process according to the invention.

EXAMPLE 1

1-(6-Thiochromanyl)-2-n-octylamino-1-propanol (a) To 35 gr. of aluminum chloride in 500 ml of 1,2-dichloroethylene, 19.7 ml of propionyl chloride are added, then slowly while stirring 36.5 gr. of thiochromone in 150 ml of 1,2-dichloroethylene, the temperature being maintained at about 10° C. After addition, the mixture is stirred for 3 hours at room temperature, then decomposed by addition of ice and hydrochloric acid.

The organic phase is separated and the aqueous phase is extracted with 1,2-dichloroethylene. The combined organic phases are dried on MgSO₄, filtered and solvent is evaporated in vacuo. The residue so obtained is solidified by addition of petroleum ether; 32.5 gr. of 6-propionyl-thiochromane are so obtained.

MP(°C.): 63–65 Yield: 69% (MP=Melting Point)

(b) To a solution of 32 gr. of 6-propionyl-thiochromane in 400 ml of anhydrous ether, 8 ml of bromine are dropwise added, temperature being maintained at ±5° C. After addition, the mixture is still stirred for 2 to 3 hours at room temperature, than an aqueous saturated NaHCO₃ solution is slowly added. The aqueous phase is twice extracted with 100 ml ether, combined organic phases are dried on MgSO₄, filtered, and solvent is evaporated in vacuo. The residue so obtained is treated with 100 ml of petroleum ether; 38 gr. of α-bromo-6-propionyl-thiochromane are obtained.

MP (°C.): 71–73. Yield 86%

(c) 20 gr. of the preceding product, 15 ml of n-octylamine and 200 ml of ethanol are refluxed for 4 hours. The mixture is cooled to ±5° C. and 5.2 gr. of sodium borohydride are gradually added. After addition, the mixture is still stirred for 1 or 2 hours at room temperature, then solvent is evaporated in vacuo. The residue is taken up with 200 ml of water and extracted with 3×100 ml of chloroform. The combined organic phases are water washed, dried on MgSO₄, filtered, and solvent is evaporated in vacuo. The residue obtained is recrystallized from acetone. 13.3 gr. of 1-(6-thiochromanyl)-2-n-octylamino-1-propanol are obtained.

MP (°C.): 115–116. Yield: 60%.

|  | Centesimal analysis: | | |
| --- | --- | --- | --- |
|  | C | H | N |
| % calculated | 71.58 | 9.91 | 4.17 |
| % found | 71.70 | 9.85 | 4.05 |

EXAMPLE 2

1-(2,3-dihydro-5-benzo b thienyl-2-(4-phenylbutylamino)-1-propanol (a) To 0.3M of aluminum chloride in 500 ml of 1,2-dichloroethylene, 0.21M of propionyl chloride are added, then slowly while stirring 0.2M of 2,3-dihydrobenzo[b]thiophene are added, temperature being maintained at about 10° C. The mixture is then still stirred for 3 hours at room temperature, then decomposed with a mixture of ice and hydrochloric acid. The organic phase is separated and the aqueous phase is extracted with 1,2-dichloroethylene. The combined organic phases are dried on MgSO₄, filtered and solvent is evaporated in a vacuum. The residence obtained is solidified by addition of petroleum ether: 25 gr. of 5-propionyl-2,3-dihydrobenzo[b]thiophene are so obtained.

MP (°C.): 50–52 Yield: 55%.

(b) To 12.5 gr. of the preceding product in 150 ml of anhydrous tetrahyrofuran, 3.3 ml of bromine are dropwise added while agitating at a temperature of ±10° C. Agitation is still continued for 1 hour at room temperature, then 50 ml of an aqueous 10% NaHCO₃ solution are added. The organic phase is separated, dried and evaporated. The oily residue obtained is solidified by addition of petroleum ether; 30 gr. of 5-(α-bromopropionyl)-2,3-dihydrobenzo[b]thiophene are obtained.

MP (°C.): 64–66

(c) 15 gr. of 5-α-bromopropionyl)-2,3-dihydrobenzo[b]thiophene, 16 gr. of 4-phenylbutylamine and 150 ml of methanol are refluxed for 3 hours. The solution is cooled to ±5° C. and 5 gr. of sodium borohydride are slowly added. After addition, stirring is still continued for 3 to 4 hours at room temperature, then solvent is evaporated in vacuum. The residence is treated with 200 ml of water and extracted with chloroform. The organic phase is water washed, dried on MgSO₄, filtered and solvent is evaporated in vacuo. The solid residue is recrystallised from acetone, 9.9 gr. of product are so obtained.

MP (°C.): 113–115 Yield: 55%

|  | Centesimal analysis | | |
| --- | --- | --- | --- |
|  | C | H | N |
| % calculated | .73.85 | 7.97 | 4.10 |
| % found | 73.50 | 7.95 | 3.90 |

EXAMPLE 3

1-(2,3,4,5-tetrahydrobenzo[b]thiepin-7-yl)-2-(4-phenylbytylamino)-1-propanol (a) To 0.27M of aluminium chloride in 500 ml of 1,2-dichloroethylene, 0.25M of propionyl chloride are added, then slowly while stirring 0.25M of 2,3,4,5-tetrahydrobenzo[b]thiepine, temperature being maintained at about 10° C. The mixture is then stirred for 3 to 4 hours at room temperature, then decomposed with a mixture of ice and hydrochloric acid. The organic phase is separated and the aqueous phase is extracted with 1,2-dichloroethylene. The combined organic phases are dried on MgSO₄, filtered and solvent is evaporated in vacuum. The residue is distilled in vacuo. 30 gr. of dense oil are obtained. Yield: 60%; boiling point: BP: 130–135 (0.4 mm). The NMR spectrum (nuclear magnetic resonance) is conform to the structure 7-propionyl-2,3,4,5-tetrahydrobenzo[b]thiepine.

(b) To 11 gr. of the preceding product in 150 ml of anhydrous tetrahydrofuran (THF), 2.6 ml of bromine are dropwise added at a temperature of ±10° C. The mixture is then still stirred for 1 hour at room temperature, then 30 ml of an aqueous 10% NaHCO₃ solution are added. The organic phase is separated, dried and evaporated. 13.2 gr. of 7-(α-bromopropionyl)-2,3,4,5-tetrahydrobenzo[b]thiepine (fluid yellow oil) are so obtained, the homogeneity of which is verified by TLC (thin layer chromatography).

(c) 10 gr. of 7-(α-bromopropionyl)-2,3,4,5-tetrahydrobenzo[b]thiepine, 150 ml of methanol and 10 gr. of 4-phenylbutylamin are refluxed for 4 hours. The solution is then cooled to ±5° C. and 4 gr. of sodium borohydride are slowly added while stirring. After addition, the mixture is allowed to stand overnight at room temperature, then solvent is evaporated in vacuo. The so obtained oily residue is treated with 200 ml of water and extracted with chloroform. The organic phase is washed with water, dried on Na₂SO₄, filtered and solvent is evaporated in vacuo. The residue so obtained is recrystallized from acetone. 7.5 gr. of product are obtained.

MP (°C.): 87–89 Yield: 53%.

|  | Centesimal analysis | | |
| --- | --- | --- | --- |
|  | C | H | N |
| % calculated | 74.74 | 8.45 | 3.79 |

|  | Centesimal analysis | | |
| --- | --- | --- | --- |
|  | C | H | N |
| % found | 74.85 | 8.65 | 3.70 |

EXAMPLE 4

1-(2-methyl-2,3-dihydrobenzo[b]thienyl)-2-[2-(chlorophenoxy)-ethylamino]-1-propanol To 0.15M of aluminum chloride, 0.11M of propionyl chloride and 150 ml of 1,2-dichloroethylene, 0.1M of 2-methyl2,3-dihydrobenzo[b]-thiophene (prepared according to method of Petropoulos, J. Am. Chem. Soc., 75, 1130, 1953) are added slowly, temperature being maintained at ±10° C. After addition, the mixture is still stirred for 3 hours at room temperature, then a mixture of ice and HCl is added. The mixture is extracted with 1,2-dichloroethylene, dried on MgSO$_4$ and solvent is evaporated. The oily residue as stripped in vacuum. 14 gr. of 5-propionyl-2-methyl-2,3-dihydrobenzo[b]thiophene are so obtained.

BP (0.2 mm): 110–115 Yield: 70% The NMR spectrum is conform to the structure.

(b) To 7 gr. of the preceding product dissolved in 100 ml of anhydrous THF, 1.8 ml of bromine are added dropwise while stirring and maintaining the temperature at about 10° C. After addition, the mixture is still stirred for 1 hour at room temperature, then an aqueous HaHCO$_3$ solution is added. The organic phase is separated, dried and evaporated. 8.5 gr. of 5-(α-bromopropionyl)-2-methyl-2,3-dihydrobenzo[b]thiophene are obtained.

MP (°C.): 52–54 Yield: 88% The NMR spectrum is conform to the structure and the product appears to be homogeneous in TLC (silica gel-C$_6$H$_6$).

(c) 16 gr. of the preceding product, 12 gr. of α-(p-chlorophenoxy)-ethylamine and 200 ml of ethanol are refluxed for 3 hours. The solution is cooled to ±5° C. and 5 gr. of NaBH$_4$ are added slowly. After addition, the mixture is still stirred for 2 to 3 hours at room temperature, solvent is evaporated and the residue is extracted with CHCl$_3$. The organic phase is dried on MgSO$_4$, filtered, evaporated and the so obtained residue is recrystallized from acetone. 5.5 gr. of product are so obtained.

MP (°C.): 108–109

|  | Centesimal analysis | | |
| --- | --- | --- | --- |
|  | C | H | N |
| % calculated | 63.56 | 6.40 | 3.70 |
| % found | 63.70 | 6.45 | 3.85 |

The structure of the product is confirmed by mass, NMR and IR spectra.

EXAMPLE 5

1-(3-methyl-6-thiochromanyl)-2-[2-(phenoxy)ethylamino]-1-propanol (a) To 0.13M of AlCl$_3$, 0.12M of propionyl chloride in 150 ml of 1,2-dichloroethylene, 0.1M (16.4 gr.) de 3-methyl-thiochromane are dropwise added at a temperature of ±5° C. After agitating the mixture for 3 hours at room temperature, a mixture of ice and HCl is added and extraction is made with CHCl$_3$. The organic phase is dried on MgSO$_4$, filtered and evaporated. 17.3 gr. of 6-propionyl-3-methyl thiochromane are so obtained, the homogeneity of which is verified by TLC and the structure of which is verified by NMR spectrum.

(b) To 22 gr. of the preceding product in 150 ml of THF, 5.2 ml of bromine are dropwise added while stirring at ±5° C. The solution is treated according to the already described method. 26 gr. of 6-(α-bromopropionyl)-3-methyl thiochromane are obtained.

MP (°C.): 60–63 (MeOH) Yield: 85% The NMR spectrum is conform to the structure.

(c) 11 gr. of the preceding product, 15 gr. of 2-phenoxyethylamine and 150 ml of ethanol are refluxed for 2 hours The mixture is cooled to ±5° C. and 6 gr. of NaBH$_4$ are slowly added. The solution is treated according to the already described method. After recrystallization from acetone, 5 gr. of product are obtained.

MP (°C.): 85–87

|  | Centesimal analysis | | |
| --- | --- | --- | --- |
|  | C | H | N |
| % calculated | 70.54 | 7.61 | 3.91 |
| % found | 70.42 | 7.60 | 3.90 |

The NMR, IR and mass spectra are conform to the structure.

EXAMPLE 6

1-(8-methyl-6-thiochromanyl)-2-n-octylamino-1-propanol (a) 165 gr. of 8-methyl-thiochromane are treated with propionyl chloride in the presence of AlCl$_3$ in 1,2-dichloroethylene according to the method already described in the preceding examples. 107.4 gr. of product are so obtained. BP: 140–155 (0.50 mm). The product solidifies.

MP (°C.): 48–51 Yield: 50% The NMR spectrum is conform to the structure.

(b) 107.4 gr. of the preceding product in 800 ml of THF are brominated with 25 ml of bromine according to the already described process. 91.7 gr. of 6-(α-bromopropionyl)-8-methyl-thiochromane are obtained.

MP (°C.).: 79–80 (Petroleum ether) Yield: 63%. The NMR spectrum is conform to the structure.

(c) 20 gr. of the preceding product, 20 gr. of n-octylamine and 300 gr. of methanol are refluxed for 4 hours. The mixture is cooled to ±0° C. and 9.5 gr. of NaBH$_4$ are slowly added. After usual treatment, 14 gr. of product are obtained.

MP (°C.): 129–130 (CHCl$_3$)

|  | Centesimal analysis | | |
| --- | --- | --- | --- |
|  | C | H | N |
| % calculated | 72.15 | 10.09 | 4.01 |
| % found | 72.05 | 9.75 | 3.85 |

The NMR, mass and IR spectra are conform to the structure.

EXAMPLE 7

1-(2-methyl-2,3-dihydro-5-benzo[b]furanyl-2-[4-(p-chlorophenyl)butylamino]-1-propanol (a) 100 gr. (0.75 mole) of 2-methyl-2,3-dihydrobenzo[b]furane are added at 10° C. and while agitating to a mixture obtained by successive addition of 108 gr. (0.8 mole) of aluminum chloride and 71.6 gr. (0.75 mole) of propionyl chloride to 1000 ml of dichloromethane. At the end of the addition, agitation is continued for 3 hours at room temperature. The final medium is formed with caution on ice mixed with a little concentrated hydrochloric acid. The organic phase is decanted, dried, then dry evaporated. The oily residue is distilled, 91.3 gr. (0.48 mole) of the cetonic derivative are collected.

BP: 119° C./0.5 Torr. The nuclear magnetic resonance spectrum is in agreement with structure.

(b) To a solution of 57 gr. (0.3 mole) of 2-methyl-5-propionyl-2,3-dihydrobenzo[b]furane in 600 ml of diethyl ether, maintained at 10° C., a trace of benzoyl peroxyde is added, then 47.9 gr. (0.3 mole) of bromine. The mixture is then stirred for 2 hours at room temperature. The final medium is washed with an aqueous 10% sodium hydrogen carbonate solution, with water. Then it is dried and dry evaporated. The solid residue is recrystallized from a 1:1 hexane/cyclohexane mixture. 67.3 gr. (0.25 mole, 83%) of brominated cetone are so obtained.

MP (°C.): 79.6. The nuclear magnetic resonance spectrum is in agreement with the expected structure.

(c) A solution of 8.2 gr. (45 moles) of p-chlorophenyl-butylamine in 100 ml of acetonitrile is stirred and refluxed. 12.4 gr. (90 mmoles) of potassium carbonate are added thereto, then over one hour a solution of 12 gr. (45 mmoles) of the preceding brominated cetone in 80 ml of acetonitrile. After the end of the addition, reflux is maintained for 1.5 hour. To the medium at room temperature, a solution of 1.8 gr. (48 mmoles) of sodium borohydride in 10 ml of water basified with a drop of 40% aqueus NaOH is dropwise added. The solid is filtered and the filtrate is dry evaporated. The residue is a solid. The latter added to the first one is recrystallized from a 1:1 hexane/cyclohexane mixture. 5.1 gr. (14 mmoles, 31%) of a product are obtained, the melting point of which being 107.8° C. The NMR spectrum confirms the expected structure.

|  | Centesimal analysis | | |
| --- | --- | --- | --- |
|  | C | H | N |
| % calculated | 70.70 | 7.60 | 3.72 |
| % found | 70.40 | 7.60 | 3.60 |

EXAMPLE 8

1-(2-methyl-6-thiochromonyl)-2-(4-phenylbutylamino)-1-propanol (a) 83 gr. (0.5M) of 2-methyl-thiochromane are treated with 43.2 ml of propionyl chloride (0.5M) in the presence of 73 gr. of AlCl₃ (0.55M) in 750 ml of 1,2-dichloroethylene in the already described preceding examples. 64 gr. of 2-methyl-6-propionyl-thiochromane are obtained.

MP (°C.): 65-66 (petroleum ether) Yield: 58%. The NMR spectrum is conform to the structure.

(b) 64 gr. of the preceding product in 500 ml of absolute methanol are treated with 14.9 ml of bromine according to the already described process. 82 gr. of 6-(α-bromopropionyl)-2-methyl-thiochromane are obtained.

MP (°C.): 78-79 Yield: 95%. The NMR spectrum is conform to the structure.

(c) 15 gr. of the preceding product, 9 gr. of 4-phenyl-butylamine and 200 ml of methanol are refluxed for 4 hours. The mixture is cooled to ±0° C. and 4 gr. of NaBH₄ are slowly added. After usual treatment and recrystallization from methanol. 6 gr. of 1-(2-methyl-6-thiochromanyl)-2-(4-phenylbutylamino)-1-propanol are obtained.

MP (°C.): 118-119. Yield: 35%

|  | Centesimal analysis | | |
| --- | --- | --- | --- |
|  | C | H | N |
| % calculated | 74.74 | 8.45 | 3.79 |
| % found | 74.80 | 8.45 | 3.70 |

The NMR, mass and IR spectra are conform to the structure

EXAMPLE 9

1-(2,3-dihydro-5-benzo[b]furanyl)-b 2-(4-phenylbutylamino)-1-propanol (a) 8.8 gr of 2,3-dihydro-6-propionylbenzo[b]furane in 50 ml of anhydrous THF are treated with 2.6 ml of bromine according with already described process. The product so obtained is recrystallized from methanol: 8 gr of 6-(α-bromopropionyl)-2,3-dihydrobenzo[b]furane are obtained.

MP (°C.): 65-66 Yield: 40%

(b) 10 gr of the preceding product, 6 gr of 4-phenyl-butylamine and 100 ml of methanol are refluxed for 3 hours. The mixture is cooled to ±0° C. and 4 gr of NaBH₄ are slowly added. After usual treatment and recrystallization from acetone, 7.7 gr of product are obtained.

MP (°C.): 131-133 Yield: 50%

|  | Centesimal analysis | | |
| --- | --- | --- | --- |
|  | C | H | N |
| % calculated | 77.49 | 8.36 | 4.30 |
| % found | 77.25 | 8.25 | 4.10 |

The NMR, mass and IR spectra are conform to the structure.

EXAMPLE 10

1-[(1,4-Benzodithien)-6-yl]-2-(4-phenylbutylamino)-1-propanol (a) To 0.12M of aluminum chloride in 250 ml of 1,2-dichloroethylene, 0.12M of propionyl chloride are added, then slowly while agitating and at a temperature of ±15° C., 0.1M of 1,4-benzoithiene in 100 ml of 1,2-dichloroethylene. After addition, the mixture is stirred for 1 hour at room temperature, then is decomposed with a mixture of ice and hydrochloric acid. After usual treatment, 12 gr of 6-propionyl-1,4-benzodithiene are obtained.

BP: 145-150 (0.2 mm) Yield: 60%

(b) At 10 gr of the preceding product dissolved in 100 ml of anhydrous THF, 2.3 ml of bromine are dropwise added while stirring at a temperature of ±10° C. After usual treatment, 11 gr of 6-(α-bromopropionyl)-1,4-benzodithiene are obtained.

MP (°C.): 72-73 Yield: 80%

(c) 10 gr of the preceding product, 100 ml of methanol and 10 gr of 4-phenylbutylamine are refluxed for 3 hours. The solution is cooled to ±50° C. and 7 gr of NaBH₄ are added. Then the solvent is evaporated, the residue is diluted with water and extraction is made with chloroform. The organic phase is dried on MgSO$_4$, filtered and evaporated. The solid so obtained is recrystallized from methanol. 7.5 gr of the final product are so obtained.

MP (°C.): 138–140 Yield: 55%

| | Centesimal analysis | | |
|---|---|---|---|
| | C | H | N |
| % calculated | 67.50 | 7.28 | 3.75 |
| % found | 67.25 | 7.45 | 4.00 |

EXAMPLE 11

1-(2,3-dihydro-5-benzo[b]thienyl)-2-(4-phenyl-butylamino)-1-propanol threo form)

4 gr of 1-(2,3-dihydro-5-benzo[b]thienyl-2-bromo-1-propanol, 100 ml of ethanol and 20 gr of 4-phenyl-butylamine are refluxed for 5 hours. The solvent and excess amine are evaporated in vacuo and the residue obtained is treated with ether. The solid is recrystallized from a mixture of methanol and ether, and the corresponding free base is obtained by treatment with a diluted NaOH solution and recrystallized from acetone. 1.05 gr of final product are so obtained.

MP (°C.): 85–87

| | Centesimal analysis | | |
|---|---|---|---|
| | C | H | N |
| % calculated: | 73.80 | 7.95 | 4.10 |
| % found: | 73.40 | 7.90 | 4.20 |

The threo configuration of the product is confirmed by examination of the NMR spectrum (JH$_1$, H$_2$=9 cps; δH$_1$=4.04 ppm; CDCl$_3$—1% TMS).

EXAMPLE 12

1-(5-indanyl)-2-(4-phenylbutylamino)-1-propanol (a) To 17.4 gr of 5-propionylindane in 100 ml of anhydrous THF, 5.12 ml of bromine (at ±10° C.) are dropwise added. The mixture is then stirred for 1 hour, at room temperature, then 100 ml of an aqueous NaHCO$_3$ solution are added.

The separated organic phase is dried on MgSO$_4$, filtered and evaporated. 13 gr of a fluid oil are so obtained, the homogeneity of which is verified in TLC and the structure of which is verified by NMR spectrum.

(b) 13 gr of the preceding product, 10 gr of 4-phenyl-butylamine and 100 ml of methanol are refluxed for 3 hours. The solution is then cooled to ±5° C. and then 6 gr of NaBH$_4$ are slowly added while stirring.

The solvent is evaporated, the mixture is diluted with H$_2$O and extracted with CHCl$_3$. The organic phase is dried, filtered, evaporated and the residue is recrystallized from acetone 4 gr of product are so obtained.

MP (°C): 108–110.

| | Centesimal analysis | | |
|---|---|---|---|
| | C | H | N |
| % calculated | 81.65 | 9.05 | 4.35 |
| % found | 81.40 | 9.05 | 4.60 |

The structure of the product is confirmed by mass, NMR and IR spectra.

EXAMPLE 13

1-[6-(1,2,3,4-tetrahydronaphthyl]-2-(4-phenyl-butylamino-1-propanol

A mixture of 21.4 gr of 6-(2-bromopropionyl)-1,2,3,4-tetrahydronaphtoluene (obtained by an acylation of tetralin by means of 2-bromopropionyl bromide; MP (°C.): 60.4°, 15 gr of 4-phenylbutylamino and 100 ml of methanol are refluxed for 3 hours. To the solution cooled to ±5° C., 12 gr of NaBH$_4$ are added. The amino-alcohol is then isolated and purified as described in Example 12. Weight: 5.3 gr. MP (°C.): 99.7°.

| | Centesimal analysis | | |
|---|---|---|---|
| | C | H | N |
| % calculated: | 81.9 | 9.3 | 4.2 |
| % found: | 81.7 | 9.3 | 3.9 |

The structure of the product is confirmed by mass, NMR and IR spectra.

EXAMPLE 14

1-(2,3-dihydro-5-benzo[b]thienyl)-2-(4-phenyl-butylamino)-1-propionyloxypropane

A mixture comprising 7 ml (7.4 gr; 80 moles) of propionyl chloride, 10 gr of 1-(2,3-dihydro-5-benzo[b]-thienyl)-2-(4-phenylbutylamino)-1-propanol hydrochloride and 10 ml of toluene is heated for 3 hours at reflux temperature. The final medium is dry evaporated under reduced pressure and the residue is recrystallized from acetonitrile.

5.9 gr of final product are so obtained, the structure of which is confirmed by examination of NMR and IR spectra.

MP (°C.): 169.9

| | Centesimal analysis | | |
|---|---|---|---|
| | C | H | N |
| % calculated: | 66.40 | 7.40 | 3.10 |
| % found: | 66.54 | 7.60 | 3.40 |

EXAMPLE 15

15 gr of 1-(2,3-dihydro-5-benzo[b]thienyl)-2-(4-phenylbutylamino)-1-propanol are dissolved in 750 ml of toluene and 150 ml of chloroform, and a stream of dry gaseous HCl is bubbled therein for 2 hours. The mixture is then still stirred for 2 hours at room temperature, the precipitate so obtained is filtered, washed with ice-cooled pentane and dried. 15 gr of hydrochloride are so obtained.

MP (°C.): 208–209.

| | Centesimal analysis | | |
|---|---|---|---|
| | C | H | N |
| % calculated: | 66.72 | 7.40 | 3.70 |
| % found: | 66.70 | 7.50 | 3.65 |

EXAMPLE 16

16 gr of 1-(6-thiochromanyl)-2-n-octylamino-1-propanol are dissolved in 600 ml of toluene and a stream of anhydrous HCl is passed through for 1.5 hours. The precipitate so obtained is filtered, washed with water-cooled pentane and dried. 17 gr of hydrochloride are obtained.

MP (°C.): 227

| | Centesimal analysis | | |
|---|---|---|---|
| | C | H | N |
| % calculated: | 64.60 | 9.15 | 3.77 |
| % found: | 64.60 | 9.15 | 3.65 |

EXAMPLE 17

2 gr of 1-(6-thiochromanyl)-2-(4-phenylbutylamino)-1-propanol are dissolved in 100 ml of anhydrous ether. A stream of dry gaseous HCl is passed through for 15 minutes, the resulting precipitate is filtered and dried. 2.1 gr of hydrochloride are so obtained.

MP (°C.): 204–205

EXAMPLE 18

28.0 gr (0.144M) of D-glucuronic acid are dissolved in 340 ml of water heated to 50° C. and 34.1 gr (0.1M) of 1-(2,3-dihydro-5-benzo[b]thienyl)-2-(4-phenylbutylamino)-1-propanol are added portionwise with vigorous stirring. Stirring is continued until dissolution is complete which requires about 20 minutes. A clear solution which can be diluted at will with distilled water is so obtained.

The melting points of compounds described in Examples, as well as of other compounds prepared according to the invention, are cited in following Table I.

Pharmacological results of a large number of compounds according to the invention are given in following Tables II and III. The results given in Table II have to be interpreted in the following manner:

(1) The acute toxicity was determined on fasted male mice. The tested substances were orally administered and LD50 values (lethal dose for 50% of animals) were calculated according to the method of Litchfield and Wilcoxon (J. Pharmacol. exp. Ther. 96, 94–113, 1949). These LD50 values are given in mg/kg and also, when possible, with their confidence limits for p=95%.

(2) The antihypertensive activity was measured on unanaesthetized, hypertension-suffering rat. The tested substances were orally given at a rate of 60 mg/kg. The systolic arterial pressure was measured every 30 minutes for 2 hours before and for 3 hours after the tested product was given. Results are expressed as follows:
O: no reduction of arterial pressure.
+: reduction lower than 10 mm Hg.
++: reduction of 10 to 20 mm Hg.
+++: reduction higher than 20 mm Hg.

(3) The vasodilator activity was measured at the level of femoral artery on anaesthetized dog (technique of perfused paw). The tested substances were given intra-arterially at the rate of 30 mg/kg. Results are expressed with respect to papaverine tested at the same dose.
O: no action.
+: slight activity.
++: effect equal to half the effect of papaverine.
+++: effect equal to that of papaverine.
++++: effect higher than that of papaverine.

(4) The antispasmodic activity was measured in vitro, on guinea-pig ileum, the contractions of which were caused by histammne (Hist.), acetylcholine (Achol) or barium chloride ($BaCl_2$). The tested products were added to perfusion bath 15 minutes before the spasm-producing agents.

The dose is given in micograms (μg) per ml of bath causing complete spasm inhibition.

The results given in Table III must be interpreted on the basis of following information. (1) Method of Campbell and Richter (Acta Pharmacol. Toxicol. 25, 345, 1967) was used. The tested substances were given intraperitoneally to male mice of 25 gr, 30 minutes before observation.

This list has for its object to determine the LD50 value by intraperitoneal way, to define animal behaviour changes and to determine minimal active dose (MAD) by this way. The LD50 and MAD values are expressed in mgr/kg. The main symptoms observed in the present case indicate a depression of central nervous system, qualitatively comparable to the effect of tranquillizers.

In tables II and III, the numbers given in column 1 correspond to numbers of column 1 of Table I. The same numbers concern the same compounds.

The products of the invention can be used in various forms.

The following Examples are not limitative and relate to galonic recipes containing, as active product designated by reference "A" hereinafter, one of the following compounds 1-(2,3-dihydro-5-benzo[b]thienyl)-2-(4-phenylbutylamino)-1-propanol; 1-(6-thiochromanyl)-2-(4-phenylbutylamino)-1-propanol; 1-(2,3,4,5-tetrahydrobenzo[b]thiepin-7-yl)-2-(4-phenylbutylamino)-1-propanol; 1-(2,3-dihydro-5-benzo[b]thienyl-2-(4-phenylbutylamino)-1-cyclohexanoyloxypropane.

| Intramuscular injection | |
|---|---|
| A | 100 mg |
| Isopropyl myristate | 0.75 ml |
| Peanut oil q.s. | 3 ml |
| A | 50 mg |
| Ethyl alcohol | 0.50 ml |
| Polyethylene glycol 400 | 0.25 ml |
| Propylene glycol | 0.50 ml |
| 10% acetic acid | 1.125 ml |
| 70% Sorbitol | 0.75 ml |
| Distilled water, q.s. | 3 ml |
| Solution for oral administration | |
| A | 5 ml |
| Ethyl alcohol | 0.1 ml |
| Propylene glycol | 0.05 ml |
| 10% acetic acid | 0.05 ml |
| Simple syrup (65% saccharose), q.s. | 1 ml |
| A | 50 mgr |
| Aerosil | 2.5 mgr |
| Corn starch | 25 mgr |
| Lecithin | 1.5 mgr |
| Methocel | 2.5 mgr |
| STA-RX | 2 mgr |
| Avicel | 6 mgr |
| A | 50 mgr |
| Corn starch | 50 mgr |
| Sodium acetate | 15 mgr |
| Magnesium stearate | 2 mgr |
| Aerosil | 3 mgr |
| Starch STA-RX 1500 | 80 mgr |
| Capsules | |
| A | 50 mgr |
| Starch STA-RX 1500 | 94 mgr |
| Magnesium stearate | 1 mgr |
| Sodium Lauryl sulfate | 5 mgr |
| A | 50 mgr |
| Microcrystalline cellulose | 70 mgr |
| Corn starch | 30 mgr |
| Peanut oil | 0.01 mgr |
| Sodium lauryl sulfate | 5 mgr |
| A | 50 mgr |
| Sodium lauryl sulfate | 5 mgr |
| Microcrystalline cellulose | 70 mgr |
| Magnesium oxide | 20 mgr |

| | |
|---|---|
| A | 50 mgr |
| Starch STA-RX 1500 | 100 mgr |
| Magnesium stearate | 1 mgr |
| Sodium lauryl sulfate | 10 mgr |
| Microcrystalline cellulose | 30 mgr |
| Aerosil | 1 mgr |
| A | 50 mgr |
| Aerosil | 2.5 mgr |
| Corn starch | 25 mgr |
| Lecithin | 1.5 mgr |
| Methocel | 2.5 mgr |
| Soluble starch | 13 mgr |
| Talc | 7 mgr |
| Suppositories | |
| A | 100 mgr |
| Whitepsol (triglycerides), q.s. | 2.3 mgr |
| A | 100 mgr |
| Syndermin GIC (triglycerides) | 200 mgr |
| Whitepsol, q.s. | 2.3 mgr |
| A | 100 mgr |
| Polyethylene glucol 6000 | 1 mgr |
| Polyethylene glycol 1540, q.s. | 2.7 mgr |
| A | 100 mgr |
| Peanut oil | 1.5 mgr |
| Soja lecithin | 5 mgr |
| 2-Octyldodecanol | 5 mgr |
| Gelatin-glycerin, q.s. for one capsule | |
| Tablets | |
| A | 50 mgr |
| Lactose | 20 mgr |
| Aerosil | 2 mgr |
| Starch STA-RX 1500 | 18 mgr |
| Calcium phosphate (CaHPO$_2$) | 25 mgr |
| Microcrystalline cellulose | 100 mgr |
| Sodium acetate | 15 mgr |
| A | 50 mgr |
| Microcrystalline cellulose | 80 mgr |
| Sodium acetate | 25 mgr |
| Auby-gel X 52 | 20 mgr |
| Corn starch | 50 mgr |
| A | 50 mgr |
| Microcrystalline | 100 mgr |
| Starch STA-RX 1500 | 99 mgr |
| Aerosil | 1 mgr |
| A | 50 mgr |
| Aerosil | 2.5 mgr |
| Corn starch | 25 mgr |
| Lecithin | 1.5 mgr |
| Methocel | 2.5 mgr |
| STA-RX | 2 mgr |
| Avicel | 6 mgr |
| A | 50 mgr |
| Corn starch | 50 mgr |
| Sodium acetate | 15 mgr |
| Magnesium stearate | 2 mgr |
| Aerosil | 3 mgr |
| Starch STA-RX 1500 | 80 mgr |

Amongst the products of the invention, the compounds having an antihypertensive activity can be used by humans, orally at daily doses of 50 to 3000 mgr.

On various studied animal species, the secondary effects which were observed for these compounds, were characterised by sedation. The latter is obtained with substantially higher doses than therapeutical doses. The ratio between active dose and sedative dose is strongly in favour of the products of the invention with respect to those ratios observed for reference products such as α-methyldopa and propanolol.

TABLE I

| N° | X | Y | n | $R_1$ | $R_2$ | $NR_3R_4$ | $R_5$ | $R_6$ | MP (°C.)(1)(4) |
|---|---|---|---|---|---|---|---|---|---|
| 1 | S | $CH_2$ | 2 | H | $CH_3$ | $-NHnC_8H_{17}$ | H | H | 115–116 (acetone) |
| 2 | S | $CH_2$ | 2 | H | $CH_3$ | $-NH-(CH_2)_4$-C$_6$H$_5$ | H | H | 131–133 (acetone) |
| 3 | S | $CH_2$ | 1 | H | $CH_3$ | $-NHnC_8H_{17}$ | H | H | 118–120 (acetone) |
| 4 | S | $CH_2$ | 2 | $2CH_3$ | $CH_3$ | $-NHnC_8H_{17}$ | H | H | 116–117 ($CH_3OH$) |
| 5 | S | $CH_2$ | 2 | $2CH_3$ | $CH_3$ | $-NH-(CH_2)_4$-C$_6$H$_5$ | H | H | 118–119 ($CH_3OH$) |
| 6 | S | $CH_2$ | 1 | H | $CH_3$ | $-NH-(CH_2)_2$-C$_6$H$_5$ | H | H | 134–137 (acetone) |
| 7 | S | $CH_2$ | 1 | H | $CH_3$ | $-NH-(CH_2)_4$-C$_6$H$_5$ | H | H | 113–115 (acetone) |
| 8 | S | $CH_2$ | 2 | H | $CH_3$ | $-NH-(CH_2)_5$-C$_6$H$_5$ | H | H | 119–120 ($CH_3OH$) |
| 9 | S | $CH_2$ | 2 | $2CH_3$ | $CH_3$ | $-NH-(CH_2)_2$-C$_6$H$_5$ | H | H | 125–126 ($CH_3OH$) |
| 10 | S | $CH_2$ | 2 | $2CH_3$ | $CH_3$ | 4-(2-methylphenyl)piperazin-1-yl | H | H | 149–151 (acetone) |

TABLE I-continued

| N° | X | Y | n | $R_1$ | $R_2$ | $-N\begin{subarray}{c}R_3\\R_4\end{subarray}$ | $R_5$ | $R_6$ | MP (°C.)[1][4] |
|---|---|---|---|---|---|---|---|---|---|
| 11 | S | $CH_2$ | 3 | H | $CH_3$ | $-NHnC_8H_{17}$ | H | H | 221-223 ($CH_3OH-Et_2O$)[2] |
| 12 | S | $CH_2$ | 3 | H | $CH_3$ | $-NH-(CH_2)_4-$C$_6$H$_5$ | H | H | 87-89 (acetone) |
| 13 | S | $CH_2$ | 2 | H | $CH_3$ | $-NH-(CH_2)_2-$C$_6$H$_5$ | H | H | 118-120 (acetone) |
| 14 | S | $CH_2$ | 3 | H | $CH_3$ | $-NH-(CH_2)_2-$C$_6$H$_5$ | H | H | 115-117 (acetone) |
| 15 | S | $CH_2$ | 2 | H | $CH_3$ | piperazinyl-(2-methylphenyl) | H | H | 165-166 (acetone) |
| 16 | S | $CH_2$ | 2 | H | $CH_3$ | $-NH-(CH_2)_2-CH(C_6H_5)_2$ | H | H | 119-120 (acetone) |
| 17 | S | $CH_2$ | 2 | H | $CH_3$ | $-NH-(CH_2)_3-$C$_6$H$_5$ | H | H | 110-111 (MeOH) |
| 18 | S | $CH_2$ | 1 | $2CH_3$ | $CH_3$ | $-NHnC_8H_{17}$ | H | H | 70-72 (MeOH) |

TABLE I-continued
| N° | X | Y | n | $R_1$ | $R_2$ | $\begin{array}{c}R_3\\|\\-N-R_4\end{array}$ | $R_5$ | $R_6$ | MP (°C.)(1)(4) |
|---|---|---|---|---|---|---|---|---|---|
| 19 | S | $CH_2$ | 1 | $2CH_3$ | $CH_3$ | —NH—$(CH_2)_4$— 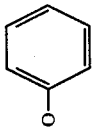 | H | H | 89-90 (MeOH) |
| 20 | S | $CH_2$ | 2 | H | $CH_3$ | —NH—$CH_2CH_2O$—  | H | H | 117-118 (acetone) |
| 21 | S | $CH_2$ | 2 | H | $CH_3$ | —NHCH$_2$CH 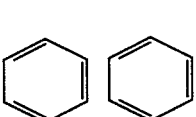 | H | H | 119-121 ($CH_3OH$) |
| 22 | S | $CH_2$ | 2 | H | $CH_3$ | —NHCH$_2$CH$_2$— 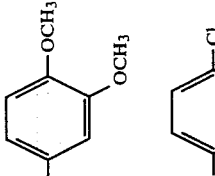 | H | H | 131-133 (acetone) |
| 23 | S | $CH_2$ | 2 | H | $CH_3$ | —NH—$(CH_2)_4$— 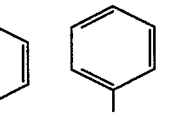 | H | H | 106-107 (acetone) |
| 24 | S | $CH_2$ | 2 | H | $CH_3$ | —NH—$(CH_2)_4O$—  | H | H | 141-144 (AcOEt) |
| 25 | S | $CH_2$ | 2 | H | $CH_3$ | —NH—$(CH_2)_4S$—  | H | H | 141-142 ($CHCl_3$) |

TABLE I-continued
| N° | X | Y | n | R₁ | R₂ | NR₃R₄ | R₅ | R₆ | MP (°C.)(1)(4) |
|---|---|---|---|---|---|---|---|---|---|
| 26 | S | CH₂ | 2 | H | CH₃ |  | H | H | 126-127 (acetone) |
| 27 | S | CH₂ | 2 | H | CH₃ | —NHcycloC₈H₁₅ | H | H | 88-89 (C₆H₆—Petroleum ether) |
| 28 | S | CH₂ | 1 | H | CH₃ | —NHcycloC₈H₁₅ | H | H | 97-99 (acetone) |
| 29 | S | CH₂ | 1 | H | CH₃ |  | H | H | 120-122 (acetone) |
| 30 | S | CH₂ | 3 | H | CH₃ |  | H | H | 90-92 (acetone) |
| 31 | S | CH₂ | 1 | H | CH₃ |  | H | H | 146-148 (MeOH—CHCl₃) |
| 32 | S | CH₂ | 1 | H | CH₃ | 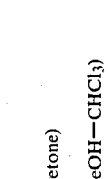 | H | H | 128-130 (MeOH) |
| 33 | S | CH₂ | 1 | H | CH₃ | —NHisoC₃H₇ | H | H | 127-129 (acetone) |
| 34 | S | CH₂ | 2 | H | CH₃ |  | H | H | 126-127 (MeOH—CHCl₃) |
| 35 | O | CH₂ | 1 | H | CH₃ |  | H | H | 131-133 (acetone) |

TABLE I-continued

| N° | X | Y | n | R₁ | R₂ | -N(R₃)(R₄) | R₅ | R₆ | MP (°C.)⁽¹⁾⁽⁴⁾ |
|---|---|---|---|---|---|---|---|---|---|
| 36 | S | CH₂ | 3 | H | CH₃ | —NH—(CH₂)₂O—C₆H₅ | H | H | 90–92 (MeOH) |
| 37 | S | CH₂ | 2 | H | CH₃ | —NH—(CH₂)₃S—C₆H₅ | H | H | 95–96 (acetone) |
| 38 | S | CH₂ | 3 | H | CH₃ | —NHisoC₃H₇ | H | H | 107–109 (acetone) |
| 39 | S | CH₂ | 3 | H | CH₃ | —NH—(CH₂)₃S—C₆H₅ | H | H | 102–104 (acetone) |
| 40 | S | CH₂ | 2 | H | CH₃ | —NH—(CH₂)₂O—C₆H₄Cl | H | H | 123–124 (acetone) |
| 41 | S | CH₂ | 2 | H | CH₃ | —NH—C₆H₁₁ | H | H | 97–98 (Hexane-Et₂O) |
| 42 | S | CH₂ | 2 | H | CH₃ | —NHCH(CH₃)—(CH₂)₃—C₆H₅ | H | H | 94–95 (Et₂O) |
| 43 | S | CH₂ | 2 | 3CH₃ | CH₃ | —NHnC₈H₁₇ | H | H | 70–72 (acetone) |
| 44 | S | CH₂ | 2 | H | CH₃ | —NH—C(CH₃)₂—C₂CH—CH₃ | H | H | 226–227 (Et₂O—MeOH)⁽²⁾ |

TABLE I-continued

| N° | X | Y | n | R₁ | R₂ | $-N\begin{smallmatrix}R_3\\R_4\end{smallmatrix}$ | R₅ | R₆ | MP (°C)(1)(4) |
|---|---|---|---|---|---|---|---|---|---|
| 45 | S | CH₂ | 2 | 3CH₃ | CH₃ | —NH—(CH₂)₄—C₆H₅ | H | H | 108–110 (acetone) |
| 46 | S | CH₂ | 2 | H | CH₃ | —NH—(CH₂)₂OCH₂—C₆H₅ | H | H | 96–98 (acetone) |
| 47 | S | CH₂ | 1 | H | CH₃ | —NH—(CH₂)₂O—C₆H₅ | H | H | 131–132 (acetone) |
| 48 | S | CH₂ | 2 | 3CH₃ | CH₃ | —NH—(CH₂)₃—C₆H₅ | H | H | 100–102 (acetone) |
| 49 | S | CH₂ | 2 | 3CH₃ | CH₃ | —NH—(CH₂)₂O—C₆H₅ | H | H | 85–87 (acetone) |
| 50 | S | CH₂ | 2 | H | CH₃ | —NH(CH₂)₃O(CH₂)₃CH₃ | H | H | 89.0 (hexane) |
| 51 | S | CH₂ | 2 | H | CH₃ | —NHcycloC₃H₅ | H | H | 96–97 (acetone) |
| 52 | S | CH₂ | 2 | H | CH₃ | —NHadamantyl-(1) | H | H | 114–115 (acetone) |
| 53 | S | CH₂ | 2 | H | CH₃ | —NH—(CH₂)₂O—C₆H₄—OCH₃ | H | H | 109–110 (acetone) |
| 54 | S | CH₂ | 2 | H | CH₃ | —NH—(CH₂)₂O—C₆H₄—CH₃ | H | H | 132–133 (acetone) |
| 55 | O | CH₂ | 1 | 2CH₃ | CH₃ | —NHnC₈H₁₇ | H | H | 94.5 (acetonitrile) |

TABLE I-continued
| N° | X | Y | n | R$_1$ | R$_2$ | $\begin{array}{c}\phantom{N}R_3\\-N\\\phantom{N}R_4\end{array}$ | R$_5$ | R$_6$ | MP (°C.)[1][4] |
|---|---|---|---|---|---|---|---|---|---|
| 56 | S | CH$_2$ | 2 | H | CH$_3$ |  —NH—(CH$_2$)$_3$—N | H | H | 101–102 (acetone) |
| 57 | S | CH$_2$ | 1 | H | CH$_3$ |  —NH—(CH$_2$)$_3$ | H | H | 128–129 (acetone) |
| 58 | S | CH$_2$ | 1 | 2CH$_3$ | CH$_3$ | 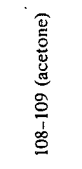 NH—(CH$_2$)$_2$O | H | H | 108–109 (acetone) |
| 59 | S | CH$_2$ | 2 | H | CH$_3$ | 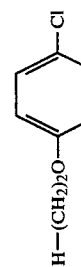 —NH—(CH$_2$)$_3$N | H | H | 258.5 (MeOH—Et$_3$O)[3] |
| 60 | S | CH$_2$ | 1 | H | CH$_3$ | 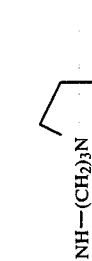 —NH—(CH$_2$)$_3$S | H | H | 109–110 (acetone) |
| 61 | S | CH$_2$ | 1 | 2CH$_3$ | CH$_3$ | 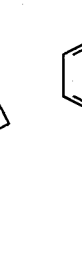 —NH—(CH$_2$)$_2$O | H | H | 109–111 (MeOH) |
| 62 | O | CH$_2$ | 1 | 2CH$_3$ | CH$_3$ |  —NH—(CH$_2$)$_3$—N | H | H | 250.8 (EtOH)[2] |

TABLE I-continued

| N° | X | Y | n | R₁ | R₂ | $\begin{array}{c}\phantom{-}R_3\\-N\\\phantom{-}R_4\end{array}$ | R₅ | R₆ | MP (°C.)[1][4] |
|---|---|---|---|---|---|---|---|---|---|
| 63 | S | CH₂ | 1 | H | CH₃ | —NHCH—(CH₂)₃—C₆H₅ <br> \| <br> CH₃ | H | H | 175–178 (MeOH—Et₂O)[2] |
| 64 | S | CH₂ | 1 | 2CH₃ | CH₃ | —NH—(CH₂)₃O—C₆H₅ | H | H | 177–179 (MeOH—Et₂O)[2] |
| 65 | O | CH₂ | 1 | 2CH₃ | CH₃ | —NH—(CH₂)₄—C₆H₄-Cl (p) | H | H | 107.8 (cyclohexane) |
| 66 | S | CH₂ | 1 | 2CH₃ | CH₃ | —NH—(CH₂)₂O—C₆H₄-OCH₃ (p) | H | H | 121–122 (acetone) |
| 67 | S | CH₂ | 1 | 2CH₃ | CH₃ | —NH—(CH₂)₃—C₆H₅ | H | H | 85–87 (Et₂O) |
| 68 | S | CH₂ | 1 | 2CH₃ | CH₃ | —NH—(CH₂)₄—C₆H₄-Cl (p) | H | H | 88–90 (Et₂O) |
| 69 | O | CH₂ | 1 | 2CH₃ | CH₃ | —NH—(CH₂)₃—C₆H₅ | H | H | 96.9 (isoPrOH—hexane) |
| 70 | O | CH₂ | 1 | 2CH₃ | CH₃ | —NH—(CH₂)₄—C₆H₅ | H | H | 110.7 (cyclohexane) |

TABLE I-continued

| N° | X | Y | n | R1 | R2 | -N(R3)(R4) | R5 | R6 | MP (°C.)[1][4] |
|---|---|---|---|---|---|---|---|---|---|
| 71 | S | $CH_2$ | 1 | $2CH_3$ | $CH_3$ | -NH-(CH$_2$)$_2$-C$_6$H$_4$-CH$_3$ (p) | H | H | 86-88 (acetone) |
| 72 | S | $CH_2$ | 2 | H | $CH_3$ | -NH-(CH$_2$)$_3$O(CH$_2$)OnC$_4$H$_9$ | H | H | 82.0 (pentane-cyclohexane) |
| 73 | S | $CH_2$ | 2 | H | $CH_3$ | -NH-(CH$_2$)$_{10}$COOCH$_3$ | H | H | 108-109 (MeOH) |
| 74 | O | $CH_2$ | 1 | $2CH_3$ | $CH_3$ | -NH-(CH$_2$)$_3$O-(CH$_2$)$_3$CH$_3$ | H | H | 152.3 (C$_6$H$_6$-cyclohexane)[2] |
| 75 | S | $CH_2$ | 2 | H | $CH_3$ | -NH-(CH$_2$)$_3$O-C$_6$H$_5$ | H | H | 113-114 (acetone) |
| 76 | S | $CH_2$ | 2 | H | $CH_3$ | -NHnC$_{14}$H$_{29}$ | H | H | 110-112 (MeOH) |
| 77 | S | $CH_2$ | 2 | H | $CH_3$ | -NH-(CH$_2$)$_3$-N(pyrrolidinone) | H | H | 102-104 (acetone) |
| 78 | S | $CH_2$ | 2 | H | $CH_3$ | -NH-(CH$_2$)$_3$-C$_6$H$_4$-Cl (p) | H | H | 84-86 (acetone) |
| 79 | S | $CH_2$ | 1 | $2CH_3$ | $CH_3$ | -NH-(CH$_2$)$_2$O-C$_6$H$_4$-CH$_3$ (p) | H | H | 129-130 (acetone) |
| 80 | S | $CH_2$ | 2 | H | $CH_3$ | -NH-(CH$_2$)$_3$S(CH$_2$)$_3$CH$_3$ | H | H | 93.6 (hexane) |
| 81 | S | $CH_2$ | 2 | H | $CH_3$ | -NH-(CH$_2$)$_3$O(CH$_2$)$_2$OCH$_3$ | H | H | 79.0 (cyclohexane) |
| 82 | O | $CH_2$ | 1 | $2CH_3$ | $CH_3$ | -NHCH(CH$_2$)$_3$-C$_6$H$_5$, CH$_3$ | H | H | 195 (isoPrOH)[2] |

TABLE I-continued
| N° | X | Y | n | R₁ | R₂ | -N(R₃)(R₄) | R₅ | R₆ | MP (°C.)[1][4] |
|----|---|---|---|----|----|-----------|----|----|----------------|
| 83 | S | CH₂ | 2 | H | CH₃ | 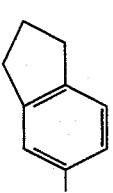  —NH—(CH₂)₂O— | H | H | 208.9 (CH₂Cl₂) |
| 84 | O | CH₂ | 1 | 2CH₃ | CH₃ | 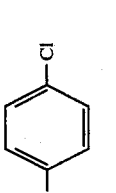  —NH—(CH₂)₂O—⟨Cl⟩ | H | H | 74 (toluene-pentane) |
| 85 | S | CH₂ | 1 | H | CH₃ | 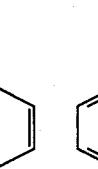  —NH—(CH₂)₂O—⟨CH₃⟩ | H | H | 86–88 (acetone) |
| 86 | S | CH₂ | 1 | H | CH₃ | 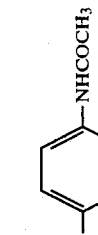  —NH—(CH₂)₂O—⟨NHCOCH₃⟩ | H | H | 119–121 (MeOH—acetone) |
| 87 | S | CH₂ | 2 | H | CH₃ | 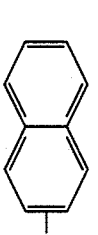  —NH—(CH₂)₂O—⟨NHCOCH₃⟩ | H | H | 120–121 (MeOH—Et₂O)[2] |
| 88 | S | CH₂ | 2 | H | CH₃ |   —NH—(CH₂)₂O— | H | H | 185.4 (H₂O) |
| 89 | O | CH₂ | 1 | 2CH₃ | CH₃ |   —NH—(CH₂)₂O— | H | H | 99.1 (cyclohexane) |
| 90 | O | CH₂ | 1 | 2CH₃ | CH₃ |   —NH—(CH₂)₄—⟨CH₃⟩ | H | H | 108.9 (cyclohexane) |

TABLE I-continued

| N° | X | Y | n | R₁ | R₂ | -NR₃R₄ | R₅ | R₆ | MP (°C.)$^{(1)(4)}$ |
|---|---|---|---|---|---|---|---|---|---|
| 91 | S | CH₂ | 2 | H | CH₃ | 4-phenylpiperidin-1-yl | H | H | 116.1 (cyclohexane) |
| 92 | S | CH₂ | 1 | H | CH₃ | —NH—(CH₂)₉—CH=CH₂ | H | H | 107–109 (methanol) |
| 93 | S | CH₂ | 2 | H | CH₃ | —NHnC₈H₁₇ | SCH₃ | H | 129–130 (CHCl₃) |
| 94 | S | CH₂ | 2 | H | CH₃ | —NH(CH₂)₄-phenyl | SCH₃ | H | 131–132 (CHCl₃) |
| 95 | S | CH₂ | 2 | H | CH₃ | —NH(CH₂)₂O-phenyl | SCH₃ | H | 136–137 (CHCl₃—Et₂O) |
| 96 | S | CH₂ | 2 | H | CH₃ | —NH(CH₂)₃S-phenyl | SCH₃ | H | 121–122 (CHCl₃—Et₂O) |
| 97 | S | CH₂ | 1 | H | CH₃ | —NHnC₈H₁₇ | H | H | 81–83 (acetone)$^{(5)}$ |
| 98 | S | CH₂ | 1 | H | CH₃ | —NH(CH₂)₄-phenyl | H | H | 85–87 (acetone)$^{(5)}$ |
| 99 | S | CH₂ | 1 | H | CH₃ | —NH(CH₂)₄-phenyl | H | COC(CH₃)₃ | 177–179 (isoPrOH)$^{(2)}$ |
| 100 | S | S | 2 | H | CH₃ | —NH(CH₂)₄-phenyl | H | H | 138–140 (MeOH) |

TABLE I-continued

| N° | X | Y | n | R₁ | R₂ | -N(R₃)(R₄) | R₅ | R₆ | MP (°C.)⁽¹⁾⁽⁴⁾ |
|---|---|---|---|---|---|---|---|---|---|
| 101 | S | S | 2 | H | CH₃ | —NHnC₈H₁₇ | H | H | 108-109 (acetone) |
| 102 | S | CH₂ | 2 | H | CH₃ | —NH(CH₂)₃CO—C₆H₄—F (p) | H | H | 181.6 (MeOH/isoPrOH)⁽²⁾ |
| 103 | S | CH₂ | 1 | H | CH₃ | —NH(CH₂)₂O—C₆H₄—NHSO₂CH₃ (p) | H | H | 160-161 (MeOH) |
| 104 | S | S | 2 | H | CH₃ | —NH(CH₂)₂O—C₆H₅ | H | H | 130-132 (CHCl₃) |
| 105 | O | CH₂ | 1 | 2CH₃ | CH₃ | —NH(CH₂)₃CO—C₆H₄—F (p) | H | H | 184.9 (MeOH/isoPrOH)⁽²⁾ |
| 106 | S | CH₂ | 1 | 2CH₃ | CH₃ | —NH(CH₂)₂S—C₆H₅ | H | H | 100-101 (MeOH) |
| 107 | S | CH₂ | 2 | H | CH₃ | —NH(CH₂)₂O—C₆H₄—C(CH₃)₃ (p) | H | H | 138.0 (hexane) |
| 108 | S | CH₂ | 1 | H | CH₃ | —NH(CH₂)₂O—C₆H₄—COC₂H₅ (p) | H | H | 176-177 (MeOH—Et₂O)⁽²⁾ |

TABLE I-continued

| N° | X | Y | n | R₁ | R₂ | -N(R₃)(R₄) | R₅ | R₆ | MP (°C.)[1][4] |
|---|---|---|---|---|---|---|---|---|---|
| 109 | S | CH₂ | 1 | 3CH₃ | CH₃ | —NH(CH₂)₄—C₆H₅ | H | H | 102–103 (MeOH) |
| 110 | S | CH₂ | 2 | H | CH₃ | morpholine with C₆H₅ and CH₃ substituents | H | H | 200.3 (MeOH/AcOEt) |
| 111 | S | CH₂ | 1 | H | CH₃ | —NH(CH₂)₃CO—C₆H₄F | H | H | 178–179 (MeOH)[2] |
| 112 | S | CH₂ | 1 | H | CH₃ | —NH(CH₂)₄—C₆H₅ | H | COCH₃ | 159.1 (acetonitrile)[2] |
| 113 | S | CH₂ | 1 | H | CH₃ | —NH(CH₂)₄—C₆H₅ | H | COCH₃ | 179.1 (MeOH/Et₂O)[5][2] |
| 114 | S | CH₂ | 2 | H | CH₃ | —NH(CH₂)₂O—C₆H₄—COOCH₃ | H | H | 113–115 (acetone) |
| 115 | S | CH₂ | 1 | H | C₂H₅ | —NH(CH₂)₄—C₆H₅ | H | H | 72–73 (MeOH) |

TABLE I-continued

| N° | X | Y | n | R₁ | R₂ | -N(R₃)(R₄) | R₅ | R₆ | MP (°C.)[1][4] |
|---|---|---|---|---|---|---|---|---|---|
| 116 | S | CH₂ | 1 | 2CH₃ | CH₃ | -NH(CH₂)₂O-C₆H₄-COC₂H₅ | H | H | 191-192 (MeOH—Et₂O)[2] |
| 117 | S | CH₂ | 1 | H | CH₃ | -NH(CH₂)₄-C₆H₅ | H | COCH(CH₃)₂ | 167.4 (acetonitrile)[2] |
| 118 | S | CH₂ | 1 | H | CH₃ | -NH(CH₂)₄-C₆H₅ | H | -COC₂H₅ | 169.9 (acetonitrile)[2] |
| 119 | S | CH₂ | 1 | H | C₂H₅ | -NHnC₈H₁₇ | H | H | 78-80 (MeOH) |
| 120 | S | CH₂ | 1 | 2CH₃ | CH₃ | -NH(CH₂)₂OCH₂-C₆H₅ | H | H | 144-145 (MeOH—Et₂O)[2] |
| 121 | O | S | 2 | H | CH₃ | -NHnC₈H₁₇ | H | H | 170-172 (MeOH)[2] |
| 122 | O | S | 2 | H | CH₃ | -NH(CH₂)₄-C₆H₅ | H | H | 95-97 (MeOH) |
| 123 | O | S | 2 | H | CH₃ | -NH(CH₂)₂O-C₆H₅ | H | H | 116-118 (MeOH) |
| 124 | O | S | 2 | H | CH₃ | -NH(CH₂)₃SnC₄H₉ | H | H | 64-65 (Et₂O—hexane) |
| 125 | S | CH₂ | 1 | H | CH₃ | -NH(CH₂)₃SnC₄H₉ | H | H | 196.2 (acetonitrile/EtOH)[2] |
| 126 | S | CH₂ | 1 | H | C₂H₅ | -NH(CH₂)₂O-C₆H₅ | H | H | 86-88 (acetone) |

TABLE I-continued

| N° | X | Y | n | R₁ | R₂ | $-N\begin{smallmatrix}R_3\\R_4\end{smallmatrix}$ | R₅ | R₆ | MP (°C)[1][4] |
|---|---|---|---|---|---|---|---|---|---|
| 127 | S | CH₂ | 2 | H | CH₃ | —NHnC₈H₁₇ | H | H | 52-53 (hexane)[5] |
| 128 | S | CH₂ | 2 | H | C₂H₅ | —NHnC₈H₁₇ | H | H | 167-168 (Et₂O—MeOH)[2] |
| 129 | S | CH₂ | 1 | H | CH₃ | —NH(CH₂)₃O(CH₂)₂OCH₃ | H | H | 152.2 (acetonitrile)[2] |
| 130 | S | CH₂ | 1 | H | CH₃ | —NH(CH₂)₄—C₆H₅ | H | COnC₃H₇ | 151.4 (acetonitrile)[2] |
| 131 | S | CH₂ | 2 | H | CH₃ | —NHnC₈H₁₇ | H | COC₂H₅ | 139.4 (AcOEt)[2] |
| 132 | S | CH₂ | 1 | H | CH₃ | —NH(CH₂)₄—C₆H₅ | H | COcycloC₄H₇ | 131.7 (AcOEt)[2] |
| 133 | S | CH₂ | 1 | H | CH₃ | —NH(CH₂)₄—C₆H₅ | H | COnC₇H₁₅ | 45.2 (acetonitrile/isoPrOH)[2] |
| 134 | S | CH₂ | 2 | H | CH₃ | —NHnC₈H₁₇ | H | COnC₃H₇ | 156.2 (AcOEt)[2] |
| 135 | S | CH₂ | 1 | H | C₂H₅ | —NH(CH₂)₄—C₆H₅ | H | H | 72-73 (MeOH) |
| 136 | S | CH₂ | 2 | H | CH₃ | —NHnC₈H₁₇ | H | COnC₇H₁₅ | 151.5 (AcOEt)[2] |
| 137 | S | CH₂ | 1 | H | CH₃ | —NH(CH₂)₄—C₆H₅ | H | COcycloC₅H₉ | 158-160 (AcOEt)[2] |
| 138 | S | CH₂ | 1 | H | CH₃ | —NH(CH₂)₄—C₆H₅ | H | COcycloC₆H₁₁ | 148-150 (acetonitrile)[2] |
| 139 | S | CH₂ | 2 | H | CH₃ | —NHnC₈H₁₇ | H | COCH(CH₃)₂ | 126.6 (AcOEt)[2] |

TABLE I-continued

| N° | X | Y | n | $R_1$ | $R_2$ | $-N\begin{smallmatrix}R_3\\R_4\end{smallmatrix}$ | $R_5$ | $R_6$ | MP (°C.)[1][4] |
|---|---|---|---|---|---|---|---|---|---|
| 140 | S | $CH_2$ | 2 | H | $CH_3$ | $-NHnC_8H_{17}$ | H | $COCH_3$ | 148.5 (AcOEt)[2] |
| 141 | S | $CH_2$ | 2 | H | $CH_3$ | $-NH(CH_2)_8CH=CH-nC_8H_{17}$ | H | H | 97–98 (acetone) |
| 142 | S | $CH_2$ | 2 | H | $CH_3$ | $-NHnC_8H_{17}$ | H | $COcycloC_5H_9$ | 156.5 (AcOEt)[2] |
| 143 | S | $CH_2$ | 2 | H | $CH_3$ | $-NHCH_2CH=C-(CH_2)_2CH=C(CH_3)_2$<br>$\quad\quad\quad\quad\quad\mid$<br>$\quad\quad\quad\quad\quad CH_3$ | H | H | 75–77 ($Et_2O$) |
| 144 | S | $CH_2$ | 2 | H | $CH_3$ | $-NHnC_8H_{17}$ | H | $COC(CH_3)_3$ | 149.4 (AcOEt)[2] |
| 145 | S | $CH_2$ | 2 | H | $CH_3$ | $-NHnC_8H_{17}$ | H | $COcycloC_4H_7$ | 144.6 (AcOEt)[2] |
| 146 | S | $CH_2$ | 2 | H | $CH_3$ | $-NHnC_8H_{17}$ | H | $COcycloC_6H_{11}$ | 182.9 (AcOEt)[2] |
| 147 | S | $CH_2$ | 2 | H | $CH_3$ | $-NHnC_{18}H_{37}$ | H | H | 122–123 ($CHCl_3$) |
| 148 | S | $CH_2$ | 1 | H | $CH_3$ | $-NH(CH_2)_2O$-(3-Cl,4-Cl-phenyl) | H | H | 118.1 (isoPrOH—hexane) |
| 149 | S | $CH_2$ | 2 | H | $CH_3$ | $-NHnC_{12}H_{25}$ | H | H | 93–101 (MeOH—$CHCl_3$) |
| 150 | S | $CH_2$ | 3 | H | $CH_3$ | $-NH(CH_2)_4$-phenyl | H | $COC_2H_5$ | 150–152 (MeOH—$Et_2O$)[2] |
| 151 | S | $CH_2$ | 1 | H | $CH_3$ | $-NH-(CH_2)_3O-C(CH_3)_2-C\equiv CH$ | H | H | 107.1 (hexane) |
| 152 | S | $CH_2$ | 2 | H | $CH_3$ | $-NH-(CH_2)_6C\equiv CH$ | H | H | 105–107 (MeOH) |
| 153 | S | $CH_2$ | 2 | H | $CH_3$ | $-NH-(CH_2)_4$-phenyl | H | H | 128–130 (MeOH—$Et_2O$)[2][5] |
| 154 | NH | $CH_2$ | 1 | H | $CH_3$ | $-NHnC_8H_{17}$ | H | H | 84–85 (acetone—$H_2O$) |
| 155 | S | $CH_2$ | 1 | H | $CH_3$ | $-NH-(CH_2)_6C\equiv CH$ | H | H | 113–115 (MeOH) |

TABLE I-continued

| N° | X | Y | n | $R_1$ | $R_2$ | $\begin{array}{c}R_3\\ \diagdown N \diagup R_4\\ \mid \end{array}$ | $R_5$ | $R_6$ | MP (°C.)[1][4] |
|---|---|---|---|---|---|---|---|---|---|
| 156 | S | $CH_2$ | 2 | H | $CH_3$ | $-NH-(CH_2-CH=\underset{CH_3}{\overset{CH_3}{C}}-CH_2)_2-CH_2-CH=\underset{CH_3}{\overset{CH_3}{C}}$ | H | H | 52–55 ($Et_2O$) |
| 157 | S | $CH_2$ | 2 | $2(CH_3)_2$ | $CH_3$ | $-NH-(CH_2)_4-$ | H | H | 121.8 ($CH_3CN$). |
| 158 | S | $CH_2$ | 2 | $2(CH_3)_2$ | $CH_3$ | $-NH-(CH_2)_2O-$ | H | H | 125.5 ($CH_3CN$) |
| 159 | NH | $CH_2$ | 1 | H | $CH_3$ | $-NH-(CH_2)_2O-$ | H | H | 90–91 ($CH_3CN-H_2O$) |
| 160 | NH | $CH_2$ | 1 | H | $CH_3$ | $-NH-(CH_2)_4-$ | H | H | 78–80 ($CH_3CN$) |
| 161 | S | $CH_2$ | 2 | 2COOH | $CH_3$ | $-NH-nC_8H_{17}$ | H | H | 125–127 (MeOH—$Et_2O$) |
| 162 | S | $CH_2$ | 2 | H | $CH_3$ | $-NH-(CH_2)_6CnC-nC_4H_9$ | H | H | 86–88 (MeOH) |
| 163 | $CH_2$ | $CH_2$ | 1 | H | $CH_3$ | $-NH-(CH_2)_4-$ | H | H | 108–110 (acetone) |
| 164 | $CH_2$ | $CH_2$ | 1 | H | $CH_3$ | $-NHnC_8H_{17}$ | H | H | 98–100 (acetone) |
| 165 | $CH_2$ | $CH_2$ | 1 | H | $CH_3$ | $-NH-(CH_2)_3-$ | H | H | 111.9 (acetonitrile) |

TABLE I-continued
| N° | X | Y | n | R₁ | R₂ | NR₃R₄ | R₅ | R₆ | MP (°C.)[1][4] |
|---|---|---|---|---|---|---|---|---|---|
| 166 | CH₂ | CH₂ | 1 | H | CH₃ | —NH—(CH₂)₄—C₆H₄—CH₃  | H | H | 126.6 (hexane) |
| 167 | CH₂ | CH₂ | 1 | H | CH₃ | —NH—(CH₂)₄—C₆H₄—Cl 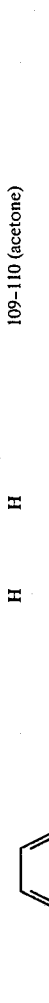 | H | H | 109–110 (acetone) |
| 168 | CH₂ | CH₂ | 1 | H | CH₃ | —NH—(CH₂)₂O—C₆H₅  | H | H | 122.2 (hexane) |
| 169 | CH₂ | CH₂ | 1 | H | CH₃ | —NH—(CH₂)₂O—C₆H₄—Cl  | H | H | 132.4 (acetone) |
| 170 | CH₂ | CH₂ | 2 | H | CH₃ | —NHnC₈H₁₇ | H | H | 97.2 (acetone) |
| 171 | CH₂ | CH₂ | 2 | H | CH₃ | —NH—(CH₂)₄—C₆H₅ 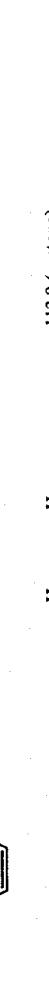 | H | H | 99.7 |
| 172 | CH₂ | CH₂ | 1 | H | CH₃ |  | H | H | 112.9 (acetone) |
| 173 | CH₂ | CH₂ | 1 | H | CH₃ | —NH—CH(CH₃)—(CH₂)₃—C₆H₅  | H | H | 213 (isoPrOH)[2] |

TABLE I-continued

| N° | X | Y | n | $R_1$ | $R_2$ | $R_3$ / $R_4$ (N-substituents) | $R_5$ | $R_6$ | MP (°C.)[1][4] |
|---|---|---|---|---|---|---|---|---|---|
| 174 | $CH_2$ | $CH_2$ | 1 | H | $CH_3$ | 4-phenylpiperidin-1-yl | H | H | 210.8 (isoPrOH)[2] |
| 175 | $CH_2$ | $CH_2$ | 1 | H | $CH_3$ | —NH(CH$_2$)$_3$CO—C$_6$H$_4$—F | H | H | 180.7 (MeOH/isoPrOH)[2] |
| 176 | $CH_2$ | $CH_2$ | 1 | H | $CH_3$ | —NH(CH$_2$)$_2$O—C$_6$H$_4$—C(CH$_3$)$_3$ | H | H | 102.2 (hexane) |
| 177 | $CH_2$ | $CH_2$ | 1 | H | $CH_3$ | 2-C$_6$H$_5$-3-CH$_3$-morpholin-4-yl | H | H | 177.1 (MeOH/AcOEt)[2] |
| 178 | $CH_2$ | $CH_2$ | 1 | H | $CH_3$ | —NH(CH$_2$)$_3$SnC$_4$H$_9$ | H | H | 82.1 (acetone) |
| 179 | $CH_2$ | $CH_2$ | 1 | H | $CH_3$ | —NH(CH$_2$)$_3$O(CH$_2$)$_2$OCH$_3$ | H | H | 134.9 (benzene-cyclohexane)[2] |
| 180 | $CH_2$ | $CH_2$ | 1 | H | $CH_3$ | —NH(CH$_2$)$_2$O—C$_6$H$_5$ | H | COCH$_3$ | 129–131 (acetonitrile)[2] |
| 181 | $CH_2$ | $CH_2$ | 1 | H | $CH_3$ | —NH(CH$_2$)$_4$—C$_6$H$_5$ | H | CO(CH$_2$)$_6$CH$_3$ | huile |
| 182 | $CH_2$ | $CH_2$ | 1 | H | $CH_3$ | —NH(CH$_2$)$_2$O—C$_6$H$_5$ | H | COCH$_3$ | 140–141 (acetonitrile)[2][5] |

[1]The recrystallization solvent is given between brackets; the melting point mentioned is that of the free base, unless contrary mention. The melting points were taken with a TOTTOLI apparatus or a METTLER FPS apparatus.
[2]Melting point of the hydrochloride.
[3]Melting point of the dihydrochloride.
[4]The elemental analyses were made for elements C, H, N and are conform to the theoretical values.
[5]Threo form.

TABLE II

| No | ACUTE TOXICITY (1) | ANTIHYPERTENSIVE ACTIVITY (2) | VASODILATOR ACTIVITY (3) | ANTISPASMODIC ACTIVITY (4) | | |
|---|---|---|---|---|---|---|
| | | | | HIST. | ACHOL | BaCl$_2$ |
| 1 | >4000 | ++ | ++++ | 3.3 | 3.3 | 1.7 |
| 2 | >4000 | +++ | ++++ | 1.7 | 8.3 | 16.7 |
| 3 | 4450 (3903-5073) | +++ | +++ | 8.3 | 16.7 | 8.3 |
| 4 | 4000 (3138-4280) | 0 | +++ | | | >16.7 |
| 5 | 3600 (3068-4212) | ++ | ++++ | | 3.3 | |
| 6 | <500 | + | +++ | | 3.3 | |
| 7 | 860 (754-980) | +++ | ++++ | 1.7 | 1.7 | |
| 8 | | 0 | ++++ | 0.8 | 1.7 | 0.8 |
| 9 | ±2750 | 0 | +++ | 3.3 | 3.3 | 0.8 |
| 10 | >4000 | +++ | ++ | 0.33 | 16.7 | 8.3 |
| 11 | 3300 (3113-3498) | +± | +++ | 0.8 | 1.7 | 3.3 |
| 12 | 5200 (2789-10880) | +++ | ++++ | 0.33 | 0.8 | 0.8 |
| 13 | | 0 | ++ | 3.3 | 0.8 | 3.3 |
| 14 | | 0 | +++ | 1.7 | 3.3 | 1.7 |
| 15 | | +++ | +++ | 0.8 | 3.3 | >16.7 |
| 16 | >4000 | ++ | +++ | 0.3 | 0.8 | 0.33 |
| 17 | >4000 | +++ | +++ | 0.8 | 1.7 | 1.7 |
| 18 | 3350 (2233-5025) | +++ | ++++ | 0.8 | 0.33 | |
| 19 | 1550 (1130-2108) | +++ | +++ | 0.8 | 1.7 | 0.8 |
| 20 | >4000 | +++ | +++ | 8.3 | 3.3 | 8.3 |
| 21 | | 0 | +++ | 0.33 | 0.33 | 1.7 |
| 22 | 3700 (3458-3959) | 0 | | 3.3 | 8.3 | 8.3 |
| 23 | ±2100 | +++ | ++++ | 0.8 | 1.7 | 0.8 |
| 24 | >4000 | 0 | +++ | 0.33 | 1.7 | 1.7 |
| 25 | >4000 | 0 | | 0.8 | 0.8 | 0.8 |
| 26 | | +++ | | 0.017 | 1.7 | 0.8 |
| 27 | | 0 | ++ | 1.7 | 1.7 | 1.7 |
| 28 | 580 (411-818) | 0 | + | 0.8 | 1.7 | 1.7 |
| 29 | 1750 (1336-2292) | +++ | ++ | 1.7 | 1.7 | |
| 30 | | +++ | +++ | 1.7 | 0.8 | |
| 31 | >4000 | 0 | | 0.17 | 1.7 | |
| 32 | 4000 (3419-4680) | +++ | | 0.8 | 1.7 | |
| 33 | 355 (317-398) | 0 | +++ | 16.7 | 16.7 | |
| 34 | ±4000 | +++ | +++ | 0.8 | 0.8 | |
| 35 | 430 (187-989) | +++ | ++ | 0.8 | 1.7 | |
| 36 | >4000 | +++ | +++ | 3.3 | 1.7 | |
| 37 | >4000 | +++ | +++ | 1.7 | 1.7 | |
| 38 | 240 (210-274) | | ++ | 3.3 | 8.3 | |
| 39 | >4000 | ++ | +++ | 1.7 | 0.8 | |
| 40 | >4000 | +++ | +++ | 1.7 | 1.7 | |
| 41 | | 0 | | 8.3 | 8.3 | |
| 42 | | +++ | +++ | 1.7 | 1.7 | |
| 43 | 3300 (2062-5280) | 0 | +++ | 0.8 | 1.7 | |
| 44 | | +++ | ++ | 16.7 | 8.3 | |
| 45 | >4000 | + | +++ | 0.8 | 0.8 | |
| 46 | 4000 (3418-4680) | 0 | +++ | 8.3 | 3.3 | |
| 47 | >4000 | ++ | ++++ | 1.7 | 1.7 | |
| 48 | >4000 | +± | | 0.8 | 1.7 | |
| 49 | ±3700 | +++ | +++ | 3.3 | 1.7 | |
| 50 | 900 (818-990) | 0 | +++ | 1.7 | 1.7 | |
| 51 | | 0 | ++ | 8.3 | 16.7 | |
| 52 | | 0 | +++ | 1.7 | 1.7 | |
| 53 | >4000 | 0 | +++ | 3.3 | 1.7 | |
| 54 | >4000 | ++ | +++ | 3.3 | 3.3 | |
| 55 | 350 (226-543) | +++ | +++ | 3.3 | 8.3 | |
| 56 | | 0 | ++ | >16.7 | >16.7 | |
| 57 | >2000 | ++ | +++ | 1.7 | 1.7 | |
| 58 | >4000 | +++ | +++ | 1.7 | 1.7 | |
| 59 | 1125 (986-1282) | 0 | +++ | 3.3 | 3.3 | |
| 60 | >2000 | +++ | +++ | 3.3 | 1.7 | |
| 61 | ±4000 | +++ | ++ | 3.3 | 3.3 | |
| 62 | 885 (799-991) | 0 | 0 | >16.7 | >16.7 | |
| 63 | 1850 (1480-2312) | +± | ++ | 0.8 | 0.8 | |
| 64 | | +++ | +++ | 1.7 | 1.7 | |
| 65 | 160 (124-206) | +++ | +++ | 0.8 | 1.7 | |
| 66 | | 0 | ++ | 1.7 | 3.3 | |
| 67 | | +++ | +++ | 1.7 | 1.7 | |
| 68 | <500 | +++ | +++ | 3.3 | 0.8 | |
| 69 | | +++ | ++ | 8.3 | 16.7 | |
| 70 | 285 (247-327) | +++ | ++ | 1.7 | 1.7 | |
| 71 | | +++ | +++ | 0.8 | 0.8 | |
| 72 | 880 (626-1232) | 0 | ++ | 1.7 | 1.7 | |
| 73 | >4000 | 0 | +++ | 3.3 | 1.7 | |
| 74 | | + | ++ | 8.3 | 8.3 | |
| 75 | >4000 | +++ | +++ | 0.8 | 1.7 | |
| 76 | >4000 | + | | | | |
| 77 | 235 (97-564) | 0 | 0 | 0.8 | 1.7 | |
| 78 | 725 (671-783) | +++ | ++++ | 0.8 | 1.7 | |
| 79 | | 0 | | 1.7 | 0.8 | |

TABLE II-continued

| No | ACUTE TOXICITY (1) | ANTIHYPERTENSIVE ACTIVITY (2) | VASODILATOR ACTIVITY (3) | ANTISPASMODIC ACTIVITY (4) | | |
|---|---|---|---|---|---|---|
| | | | | HIST. | ACHOL | BaCl$_2$ |
| 80 | 5000 (4065–6150) | +++ | ++ | 0.8 | 1.7 | |
| 81 | | +++ | ++ | 16.7 | 16.7 | |
| 82 | | 0 | ++ | 0.3 | 1.7 | |
| 83 | >4000 | 0 | +++ | 1.7 | 0.8 | |
| 84 | 1200 (952–1518) | +++ | +++ | 8.3 | 3.3 | |
| 85 | | +++ | +++ | 8.3 | 16.7 | |
| 86 | 1425 (1319–1539) | +± | +++ | 1.7 | 16.7 | |
| 87 | | 0 | +++ | 8.3 | 16.7 | |
| 88 | >4000 | 0 | +++ | 1.7 | 1.7 | |
| 89 | 550 (500–505) | +++ | +++ | 8.3 | 8.3 | |
| 90 | | +++ | ++++ | 0.8 | 1.7 | |
| 91 | | +± | +++ | 0.8 | 1.7 | |
| 92 | >4000 | ++ | | 16.7 | 16.7 | |
| 93 | >4000 | 0 | | 0.8 | 0.8 | |
| 94 | >4000 | +++ | +++ | 0.8 | 0.8 | |
| 95 | >4000 | +++ | | | | |
| 96 | >4000 | +++ | | 0.8 | 1.7 | |
| 97 | | ± | | | | |
| 98 | | + | | | | |
| 99 | | 0 | | 8.3 | 1.7 | |
| 100 | >2000 | +++ | ++++ | 8.3 | 1.7 | |
| 101 | | ++ | +++ | 0.8 | 0.8 | |
| 102 | >4000 | +++ | ++ | 0.8 | 0.3 | |
| 103 | | 0 | | 3.3 | 16.7 | |
| 104 | >4000 | +++ | | 8.3 | 16.7 | |
| 105 | ±360 | +++ | +++ | 3.3 | 3.3 | |
| 106 | >4000 | ++ | +++ | 1.7 | 1.7 | |
| 107 | >4000 | 0 | +++ | 0.8 | 0.8 | |
| 108 | >4000 | ++ | +++ | 0.8 | 3.3 | |
| 109 | ±2750 | +++ | +++ | 0.17 | 0.8 | |
| 110 | | + | 0 | 0.8 | 3.3 | |
| 111 | ±700 | ++ | +++ | 0.3 | 0.8 | |
| 112 | | +++ | +++ | 0.3 | 3.3 | |
| 113 | | + | | | | |
| 114 | >2000 | 0 | +++ | 0.8 | 3.3 | |
| 115 | ±2500 | +++ | +++ | 0.8 | 1.7 | |
| 116 | >4000 | ++ | ++ | 0.17 | 3.3 | |
| 117 | 2200 (1294–3740) | +++ | ++++ | 1.7 | 0.8 | |
| 118 | 2020 (1897–2151) | +++ | ++ | 0.8 | 1.7 | |
| 119 | 1800 (1171–2790) | 0 | ++++ | 0.3 | | |
| 120 | ±1450 | ++ | +++ | 0.8 | | |
| 121 | | 0 | +++ | 0.8 | | |
| 122 | 1650 (1375–1980) | +++ | ++++ | 0.3 | | |
| 123 | >4000 | +++ | ++++ | 0.8 | | |
| 124 | | 0 | ++ | 1.7 | | |
| 125 | 3400 (3063–3774) | 0 | ++ | 1.7 | | |
| 126 | >4000 | +++ | | | | |
| 127 | | 0 | | | | |
| 128 | >4000 | | | | | |
| 129 | 250 (176–355) | +++ | | | | |
| 130 | 3700 (2242–6105) | +++ | | | | |
| 131 | >4000 | + | | | | |
| 132 | 1900 (1496–2413) | +++ | | | | |
| 133 | 2600 (1926–3510) | +++ | | | | |
| 134 | >4000 | +++ | | | | |
| 135 | >4000 | ++ | | | | |
| 136 | >4000 | 0 | | | | |
| 137 | ±1750 | +++ | | | | |
| 138 | >4000 | +++ | | | | |
| 139 | | +++ | | | | |
| 149 | | 0 | | | | |
| 147 | | 0 | | | | |
| 153 | | ± | | | | |
| 163 | 800 (533–1200) | +++ | ++ | 1.7 | 0.8 | |
| 164 | 1750 (1129–2713) | ++ | +++ | 0.8 | 0.8 | |
| 165 | 3800 (3699–3914) | +++ | +++ | 1.7 | 1.7 | |
| 166 | | ++ | +++ | 0.8 | 0.8 | |
| 167 | ±270 | +++ | +++ | 0.8 | 0.8 | |
| 168 | >2000 | +++ | ++++ | 3.3 | 3.3 | |
| 169 | >4000 | +++ | +++ | 3.3 | 0.8 | |
| 170 | ±2300 | 0 | +++ | 1.7 | 0.8 | |
| 171 | | + | +++ | 0.8 | 0.8 | |
| 172 | 1900 (1310–2755) | +++ | ++++ | 0.08 | 1.7 | |
| 173 | 2600 (1838–3692) | 0 | ++ | 0.8 | 0.8 | |
| 174 | 2150 (1720–2687) | +± | +++ | 0.8 | | |
| 175 | | +++ | ++ | 0.8 | 0.8 | |
| 176 | >4000 | 0 | +++ | 0.17 | 0.8 | |
| 177 | | ++ | ± | 1.7 | 1.7 | |
| 178 | 870 (833–909) | ++ | +++ | 1.7 | | |

| No | ACUTE TOXICITY (1) | ANTIHYPERTENSIVE ACTIVITY (2) | VASODILATOR ACTIVITY (3) | ANTISPASMODIC ACTIVITY (4) | | |
|---|---|---|---|---|---|---|
| | | | | HIST. | ACHOL | BaCl$_2$ |
| 179 | 250 (179–350) | +++ | | | | |

We claim:

1. Amino-alcohol derivative having the formula:

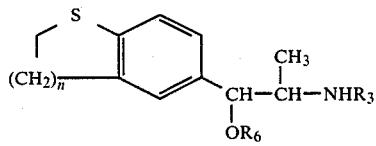

wherein:

$R_3$ is a linear or branched alkyl radical ($C_6$–$C_{10}$) or a linear or branched alkyl group ($C_2$–$C_3$) substituted by a phenoxy or a phenylthio radical or a linear or branched alkyl group ($C_3$–$C_4$) substituted by a phenyl or a benzoyl radical; said phenoxy, phenylthio, phenyl and benzoyl radicals can be substituted by a halogen or a methyl, $R_6$ is hydrogen or a linear or branched alkanoyl($C_1$–$C_4$) radical or a cycloalkanoyl($C_3$–$C_6$) radical, and n is equal to 1,2 or 3.

2. The amino-alcohol derivative of claim 1 wherein $R_3$ is a linear or branched alkyl radical ($C_6$–$C_{10}$) or a linear or branched alkyl radical ($C_2$–$C_3$) substituted by phenoxy or a linear or branched alkyl group ($C_3$–$C_4$) substituted by phenyl, and n is equal to 1 or 2.

3. 1-(6-thiochromanyl)-2-n-octylamino-propanol.

4. 1-(2,3-dihydro-5-benzo[b]thienyl)-2-(4-phenylbutylamino)-1-propanol.

* * * * *